United States Patent
Buck et al.

(10) Patent No.: US 9,931,393 B2
(45) Date of Patent: Apr. 3, 2018

(54) IMMUNOGENIC JC POLYOMAVIRUS COMPOSITIONS AND METHODS OF USE

(71) Applicant: THE UNITED STATES OF AMERICA, AS REPRESENTED BY THE SECRETARY, DEPARTMENT OF HEALTH AND HUMAN SERVICES, Washington, DC (US)

(72) Inventors: Christopher B. Buck, Bethesda, MD (US); Upasana Ray, Bethesda, MD (US); Diana V. Pastrana, Arlington, VA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/106,074

(22) PCT Filed: Dec. 19, 2014

(86) PCT No.: PCT/US2014/071621
§ 371 (c)(1),
(2) Date: Jun. 17, 2016

(87) PCT Pub. No.: WO2015/095770
PCT Pub. Date: Jun. 25, 2015

(65) Prior Publication Data
US 2016/0317643 A1 Nov. 3, 2016

Related U.S. Application Data

(60) Provisional application No. 61/919,043, filed on Dec. 20, 2013.

(51) Int. Cl.
*A61K 39/12* (2006.01)
*C07K 14/025* (2006.01)
*G01N 33/569* (2006.01)
*A61K 39/00* (2006.01)

(52) U.S. Cl.
CPC ............ *A61K 39/12* (2013.01); *C07K 14/025* (2013.01); *G01N 33/56983* (2013.01); *A61K 2039/5258* (2013.01); *A61K 2039/53* (2013.01); *A61K 2039/545* (2013.01); *A61K 2039/55505* (2013.01); *A61K 2039/58* (2013.01); *C12N 2710/22023* (2013.01); *C12N 2710/22034* (2013.01); *G01N 2333/025* (2013.01); *G01N 2469/20* (2013.01); *G01N 2800/28* (2013.01); *G01N 2800/50* (2013.01)

(58) Field of Classification Search
CPC ............ A61K 2300/00; A61K 39/0011; A61K 2039/55516; A61K 35/76; A61K 38/162; A61K 39/12; C07K 14/005; C12N 7/00; C12N 15/86; C12N 2710/22011; C12N 2710/22021; C12N 2710/22022
See application file for complete search history.

(56) References Cited

U.S. PATENT DOCUMENTS

| | | | |
|---|---|---|---|
| 6,238,859 B1 | 5/2001 | Lüke et al. | |
| 2007/0026503 A1 | 2/2007 | Lacey | |
| 2014/0154284 A1* | 6/2014 | Buck | G01N 33/56983 424/186.1 |

FOREIGN PATENT DOCUMENTS

| | | |
|---|---|---|
| WO | WO 2008/091398 | 7/2008 |
| WO | WO 2010/090757 | 8/2010 |
| WO | WO 2013/012866 | 1/2013 |
| WO | WO 2013/014134 | 1/2013 |
| WO | WO 2013/142300 | 9/2013 |

OTHER PUBLICATIONS

Jelcic I, Aly L, Binder TM, Jelcic I, Bofill-Mas S, Planas R, Demina V, Eiermann TH, Weber T, Girones R, Sospedra M, Martin R. T cell epitope mapping of JC polyoma virus-encoded proteome reveals reduced T cell responses in HLA-DRB1*04:01+ donors. J Virol. Mar. 2013;87(6):3393-408. Epub Jan. 9, 2013.*
Alhydrogel® Adjuvant 2%. InvivoGen Catalog # vac-alu-250. Aug. 6, 2011. http://www.invivogen.com/PDF/Alhydrogel_TDS.pdf.*
Buck, "Development of Vaccines Against Polyomavirus," *5th International Conference on Polyomaviruses and Human Diseases, Basic and Clinical Perspectives* (seminar presentation), May 9-11, 2013 (67 pages).

(Continued)

*Primary Examiner* — Rachel B Gill
(74) *Attorney, Agent, or Firm* — Klarquist Sparkman, LLP

(57) ABSTRACT

Methods of eliciting an immune response to a JC polyomavirus (JCV) by administering an effective amount of an immunogenic composition including an isolated JCV VP1 polypeptide or a nucleic acid encoding the VP1 polypeptide to a subject are provided. VP1 polypeptides and immunogenic compositions suitable for use in the methods are provided, including JCV genotype 2 VP1 polypeptides and/or JCV genotype 3 polypeptides. Methods of identifying a subject at risk of developing progressive multifocal leukoencephalopathy (PML) are also provided. In some embodiments, the methods include obtaining a biological sample from a subject, detecting presence or absence of JCV neutralizing antibodies in the sample from the subject, and identifying that the subject is at risk of developing PML if there is an absence of detectable JCV neutralizing antibodies in the sample from the subject.

31 Claims, 9 Drawing Sheets

(56) References Cited

OTHER PUBLICATIONS

Baksh et al., "Molecular Genotyping of BK and JC Viruses in Human Polyomavirus-Associated Interstitial Nephritis After Renal Transplantation," *Am. J. Kidney Dis.* vol. 38, No. 2, pp. 354-365, 2001.
Bloomgren et al., "Risk of Natalizumab-Associated Progressive Multifocal Leukoencephalopathy," *N. Engl. J. Med.*, vol. 366, pp. 1870-1880, 2012.
Buck, *NCI Funded Research Portfolio*, ZIABC011460, available on the World Wide Web at http://fundedresearch.cancer.gov/nciportfolio/search/details;jsessionid=CBF5AFA3DB58011B4A0AB86E0FE27241?action=abstract&grantNum=ZIABC011460&grantID=29696&grtSCDC=FY%202012&absID=29696&absSCDC=PUB2012, 2012 (1 page).
Buck, "Polyomavirus Vaccines: Easy to Make, Amazingly Immunogenic, and Possibly Life-Saving," University of North Carolina, Sep. 3, 2013 (seminar presentation; 120 pages).
Cubitt et al., "Predicted amino acid sequences for 100 JCV strains," *Journal of NeuroVirology*, vol. 7, pp. 339-344, 2001.
Ferenczy et al. "Molecular Biology, Epidemiology, and Pathogenesis of Progressive Multifocal Leukoencephalopathy, the JC Virus-Induced Demyelinating Disease of the Human Brain," *Clinical Microbiology Reviews*, vol. 25, No. 3, pp. 471-506, 2012.
Goldmann et al., "Molecular Cloning and Expression of Major Structural Protein VP1 of the Human Polyomavirus JC Virus: Formation of Virus-Like Particles Useful for Immunological and Therapeutic Studies," *Journal of Virology*, vol. 73, No. 5, pp. 4465-4469, 1999.
Gorelik et al, "Progressive Multifocal Leukoencephalopathy (PML) Development Is Associated With Mutations in JC Virus Capsid Protein VP1 That Change Its Receptor Specificity," *Journal of Infectious Diseases*, vol. 204, pp. 103-114, 2011.
Katona, "JCV vaccination could reduce the risk of developing cognitive decline, dementia, strokes and brain tumours, by preventing chronic JCV cerebral infection, and recurrent reactivation," *Medical Hypotheses*, vol. 73, pp. 268, 2009.
Maginnis et al., "Progressive Multifocal Leukoencephalopathy-Associated Mutations in the JC Polyomavirus Capsid Disrupt Lactoseries Tetrasaccharide c Binding," *mBio*, vol. 4, No. 3, e00247-13, 2013 (11 pages).
Pastrana et al., "BK Polyomavirus Genotypes Represent Distinct Serotypes with Distinct Entry Tropism," *J. Virol.* vol. 87, pp. 10105-10113, 2013.
Ray et al., "Antibody-Mediated Neutralization of PML-Associated JCV Mutants," *Progressive Multifocal Leukoencephalopathy Conference*, Jun. 19-20, 2013 (Abstract; 1 page).
Reid et al, "Sequencing and Analysis of JC Virus DNA From Natalizumab-Treated PML Patients," *Journal of Infectious Diseases*, vol. 204, pp. 237-244, 2011.
Sospedra et al., "Treating progressive multifocal leukoencephalopathy with interleukin 7 and vaccination with JC virus capsid protein VP1," *Clinical Infections Diseases*, vol. 59, No. 11, pp. 1588-1592, 2014.
Yanagihara et al., "JC Virus Genotypes in the Western Pacific Suggest Asian Mainland Relationships and Virus Association with Early Population Movements," *Human Biology*, vol. 74, No. 3, pp. 473-488, 2002.
Youssef et al., "Anti-JCV Neutralizing Antibodies as a Potential Therapy for the Treatment of PML," *Journal of Neurovirology*, vol. 18, No. Suppl. 1, p. S125, 2012.

\* cited by examiner

FIG. 1

| | | |
|---|---|---|
| 1 MAPTKRKGERKDPVQVPKLLIRGGVEVLEVKTGVDSITEVECFLTPEMGDPDEHLRGFSK |
| 1 MAPTKRKGERKDPVQVPKLLIRGGVEVLEVKTGVDSITEVECFLTPEMGDPDEHLRGFSK |
| 1 MAPTKRKGERKDPVQVPKLLIRGGVEVLEVKTGVDSITEVECFLTPEMGDPDEHLRGFSK |

| 61 SISISDTFESDSPNKDMLPCYSVARIPLPNLMEDLTCGNILMWEAVTLKTEVIGVTLMN |
| 61 SISISDTFESDSPNKDMLPCYSVARIPLPNLMEDLTCGNILMWEAVTLKTEVIGVTTLMN |
| 61 SISISDTFESDSPNKDMLPCYSVARIPLPNLMEDLTCGNILMWEAVTLKTEVIGVTTLMN |

| 121 VHSNGQATHDNGACKPVQGTSFHFFSVGGEALELQGVFNYRTKYPDGTIFPKMATVQSQ |
| 121 VHSNGQATHDNGAGKPVQGTSFHFFSVGGEALELQGVFNYRTKYPDGTIFPKMATVQSQ |
| 121 VHSMGQATHDNGAKPVQGTSFHFFSVGGEALELQGVVFNYRTYPDGTIFPKMATVQSQ |

| 181 VMNTEHKAYLDKNKAYPVECWFPDPTRNENTRYFGTLTGGENVPPVLHITNTATTVLLDE |
| 181 VMNTEHKAYLDKNKAYPVECWFPDPTRNENTRYFGTLTGGENVPPVLHITNTATTVLLDE |
| 181 VMNTEHKAYLDKNKAYPVECWFPDPTRNENTRYFGTLTGGENVPPVLHITNTATTVLLDE |

| 241 FGVGPLCKGDNLYLSAVDVCGMFTNRSGSQQWRGLSRYFKVQLRKRVKNPYPISFLLTD |
| 241 FGVGPLCKGDNLYLSAVDVCGMFTNRSGSQQWRGLSRYFKVQLRKRVKNPYPISFLLTD |
| 241 FGVGPLCKGDNLYLSAVDVCGMFTNRSGSQQWRGLSRYFKVQLRKRVKNPYPISFLLTD |

| 301 LINRRTPRVDGQPMTGMDAQVEEVRVFEGTEELPGDPDMRYVLYGQLQTKML |
| 301 LINRRTPRVDGQPMTGMDAQVEEVRVFEGTEELPGDPDMRYVDRYGQLQTKML |
| 301 LINRRTPRVDGQPMYGMDAQEEVRVFEGTELPGDPDMRYVDRYGQLQTKML |

Spearman r = 0.93
P = < 0.0001

Spearman r = 0.96
P = < 0.0001

FIG. 5A
Neutralization of 5029m

| VLP immunogen | EC₅₀ (prime) | EC₅₀ (boost) |
|---|---|---|
| 2A | 2.6 | |
| | 2.7 | |
| | | |
| | 2.8 | |
| 2A-267F | 1.7 | |
| | 1.7 | |
| | 1.7 | |
| | 1.7 | |
| | 1.7 | |
| 3B | 2.1 | |
| | 2.6 | |
| | | |
| | 2.3 | |
| 3B-55F | 1.7 | 2.9 |
| | 1.7 | |
| | 2.2 | |
| | 1.7 | |
| | 2.4 | |
| 3B-267F | 1.7 | 2.3 |
| | 2.1 | 2.5 |
| | | |
| | 2.7 | |
| | 2.2 | |

FIG. 5B
Neutralization of 2A-269F

| VLP immunogen | EC₅₀ (prime) | EC₅₀ (boost) |
|---|---|---|
| 2A-267F | 3.0 | |
| | 3.0 | |
| | | |
| | 2.7 | |
| | 2.4 | |
| 3B | 2.8 | |
| | 2.4 | |
| | | |
| | 2.7 | |
| 3B-55F | 2.0 | |
| | 1.7 | |
| | 2.3 | |
| | 2.2 | |
| | 2.3 | |
| 3B-267F | 1.7 | |
| | 1.7 | |
| | | |
| | 2.4 | |
| | 2.4 | |

FIG. 5C
Neutralization of 5147m

| VLP immunogen | EC₅₀ (prime) | EC₅₀ (boost) |
|---|---|---|
| 2A | 2.9 | 2.9 |
| | 2.9 | |
| | | |
| | | |
| 2A-267F | 2.3 | |
| | 1.7 | |
| | 2.5 | |
| | 1.9 | |
| | 2.1 | |
| 3B | 2.1 | |
| | 2.3 | |
| | 3.1 | |
| | 1.8 | |
| 3B-55F | 1.7 | |
| | 1.7 | |
| | 2.0 | 2.9 |
| | 1.7 | |
| | 1.7 | 2.5 |
| 3B-267F | 1.7 | 2.3 |
| | 1.7 | 2.4 |
| | | |
| | 1.7 | 2.4 |
| | 1.7 | |

FIG. 5D
Neutralization of 5031mb

| VLP immunogen | EC50 (prime) | EC50 (boost) |
|---|---|---|
| 2A-269F | 2.9 | |
| | 1.7 | |
| | 2.3 | |
| | 1.7 | |
| | 1.7 | |

Weeks after PML diagnosis

Weeks after PML diagnosis

IMMUNOGENIC JC POLYOMAVIRUS COMPOSITIONS AND METHODS OF USE

CROSS REFERENCE TO RELATED APPLICATION

This is the §371 U.S. National Stage of International Application No. PCT/US2014/071621, filed Dec. 19, 2014, which was published in English under PCT Article 21(2), which in turn claims the benefit of U.S. Provisional Application No. 61/919,043, filed Dec. 20, 2013, which is incorporated herein by reference in its entirety.

FIELD

This disclosure relates to compositions and methods for eliciting an immune response to JC polyomavirus, particularly monovalent JC polyomavirus capsid polypeptide immunogenic compositions.

BACKGROUND

JC polyomavirus (JCV or JCPyV) is a non-enveloped DNA virus that chronically infects the urinary tract of most adults. Although JCV is not known to cause noticeable symptoms in healthy subjects, the virus can cause a lethal brain disease, progressive multifocal leukoencephalopathy (PML), in immunosuppressed individuals. The incidence of JCV-induced PML increased dramatically during the AIDS epidemic, affecting roughly 1-3% of human immunodeficiency virus (HIV) seropositive individuals (Major, *Cleve. Clin. J. Med.* 78(Suppl 2):53-7, 2011). The availability of highly active antiretroviral therapy (HAART) has dramatically reduced the lethality of PML; however, its debilitating symptoms remain a significant risk for HIV-infected individuals (Simpson, *Cleve. Clin. J. Med.* 78(Suppl 2):524-27, 2011).

In recent years, JCV-induced PML has increasingly been found in patients treated with immunosuppressive drugs, including a variety of new monoclonal antibody therapeutics such as natalizumab and rituximab (Weissert, *J. Neuroimmunol.* 231:73077, 2011; Novak et al., *Arch. Neurol.* 65:1162-1165, 2008; Major, *N. Engl. J. Med.* 361:1041-1043, 2009; Major, *Ann. Rev. Med.* 61:35-47, 2010). An apparent common feature of HIV infection and PML-associated immunosuppressive therapies is the induction of decreased cell-mediated immunity within the central nervous system (CNS). Decreased T cell surveillance presumably allows JCV to emerge from latency and initiate a spreading infection within the CNS (Gheuens et al., *Ann. Rev. Pathol.* 8:189-215, 2013). Recent reports have found a unique spectrum of mutations in the VP1 gene of JCV strains found in PML patients (Gorelik et al., *J. Infect. Dis.* 204:103-114, 2011; Reid et al., *J. Infect. Dis.* 204:237-244, 2011), leading to speculation that the VP1 mutations might be involved in PML pathogenesis. The VP1 mutations associated with PML are not detected in urine (where JCV is typically shed); thus, JCV sequences found in urine are defined in the field as "wild-type." There remains a need for compositions and methods to prevent or inhibit JCV infection or the development of PML (or both) in vulnerable subjects.

SUMMARY

Disclosed herein are methods and compositions for eliciting an immune response against JCV and for treating or inhibiting JCV-associated pathologies, such as PML. In contrast to previous reports from the field, the inventors have unexpectedly discovered that administration of an immunogenic composition with a polypeptide (such as a VP1 polypeptide) from a single WT JCV isolate elicits an immune response (for example, a neutralizing antibody response) against multiple JCV genotypes (such as two or more JCV genotypes), including JCV genotypes with VP1 polypeptides including one or more mutations associated with PML. Also unexpectedly, immunogenic compositions based on PML-derived mutant JCV VP1 polypeptides were less effective than WT based compositions for eliciting neutralizing antibody responses. Thus, in some embodiments, the methods disclosed herein include administering to a subject a monovalent JCV VP1 polypeptide immunogenic composition (such as one based on WT JCV isolates or genotypes).

In some embodiments, the disclosed methods include administering to a subject an effective amount of an immunogenic composition based on a WT (for example, urine-derived JCV genotype) VP1 polypeptide. In particular embodiments, the methods include administering to a subject an immunogenic composition including a WT JCV genotype 2 VP1 polypeptide (such as a WT JCV genotype 2A, 2B, or 2C VP1 polypeptide), an isolated WT JCV genotype 3 VP1 polypeptide (such as a WT JCV genotype 3A or 3B VP1 polypeptide), or a combination thereof, thereby eliciting an immune response to JCV in the subject. In other embodiments, the methods include administering to a subject an effective amount of an immunogenic composition including an isolated nucleic acid encoding a JCV VP1 polypeptide based on a WT JCV isolate (for example, encoding a JCV genotype 2 VP1 polypeptide, a JCV genotype 3 VP1 polypeptide, or a combination thereof). In other embodiments, the methods include administering to a subject an effective amount of an isolated JCV genotype 1 (such as genotype 1A or 1B), 4, 5, 6, 7, or 8 VP1 polypeptide, or a combination of two or more thereof, or one or more nucleic acids encoding the VP1 polypeptides. In still further embodiments, the methods include administering to a subject an immunogenic composition including a WT JCV genotype 2 VP1 polypeptide (such as a WT JCV genotype 2A, 2B, or 2C VP1 polypeptide), an isolated WT JCV genotype 3 VP1 polypeptide (such as a WT JCV genotype 3A or 3B VP1 polypeptide), an isolated WT JCV genotype 1 VP1 polypeptide (such as a WT JCV genotype 1A or 1B VP1 polypeptide), or a combination thereof, thereby eliciting an immune response to JCV in the subject.

In some examples, the immunogenic composition consists essentially of an isolated JCV VP1 polypeptide (such as an isolated JCV genotype 2 VP1 polypeptide and/or an isolated JCV genotype 3 VP1 polypeptide), or a nucleic acid encoding the polypeptide. In one particular example, the immunogenic composition is a monovalent immunogenic composition. VP1 polypeptides suitable for use in the methods and immunogenic compositions are disclosed herein, including JCV genotype 2 VP1 polypeptides (such as polypeptides with at least 99% identity to SEQ ID NOs: 1 and 9) and JCV genotype 3 VP1 polypeptides (such as polypeptides with at least 99% identity to SEQ ID NO: 2), or nucleic acids encoding the VP1 polypeptides. In some examples, the VP1 polypeptide is included in a virus-like particle (VLP) or a pentameric VP1 capsomer. Immunogenic compositions including an isolated JCV VP1 polypeptide (for example, an isolated JCV genotype 2 VP1 polypeptide, an isolated JCV genotype 3 VP1 polypeptide, or a combination thereof) are also disclosed herein.

Also disclosed are methods of identifying a subject at risk of developing PML. In some embodiments, the methods include obtaining a biological sample from a subject (such as an immunocompromised subject, a subject infected with HIV, or a subject who has been treated with or is a candidate for treatment with an immunosuppressant), detecting presence or absence of JCV neutralizing antibodies in the sample from the subject, and identifying that the subject is at risk of developing PML if there is an absence of detectable JCV neutralizing antibodies in the sample from the subject (for example, there is an absence of detectable antibodies capable of neutralizing one of more WT or PML-associated mutant JCV genotypes). In some examples, the methods further include administering an immunogenic composition including a JCV VP1 polypeptide (such as a JCV genotype 2 and/or JCV genotype 3 VP1 polypeptide) to a subject identified as being at risk for developing PML.

The foregoing and other features of the disclosure will become more apparent from the following detailed description, which proceeds with reference to the accompanying figures.

BRIEF DESCRIPTION OF THE DRAWINGS

FIG. 1 is an alignment of exemplary wild type (WT) JCV genotype 1 (1A; SEQ ID NO: 10), 2 (2A; SEQ ID NO: 1), and 3 (3B; SEQ ID NO: 2) VP1 polypeptide sequences.

FIG. 2A shows serum samples titered for neutralization of WT JCV genotype 2 (labeled 2A) using either ART or SFT cells. Similar neutralizing titer values for each serum sample were observed using either cell line. FIG. 2B shows that the sera had similar neutralizing titers for JCV genotypes 2 (labeled 2A) and 3 (labeled 3B) pseudoviruses using SFT cells.

Figure 2A:
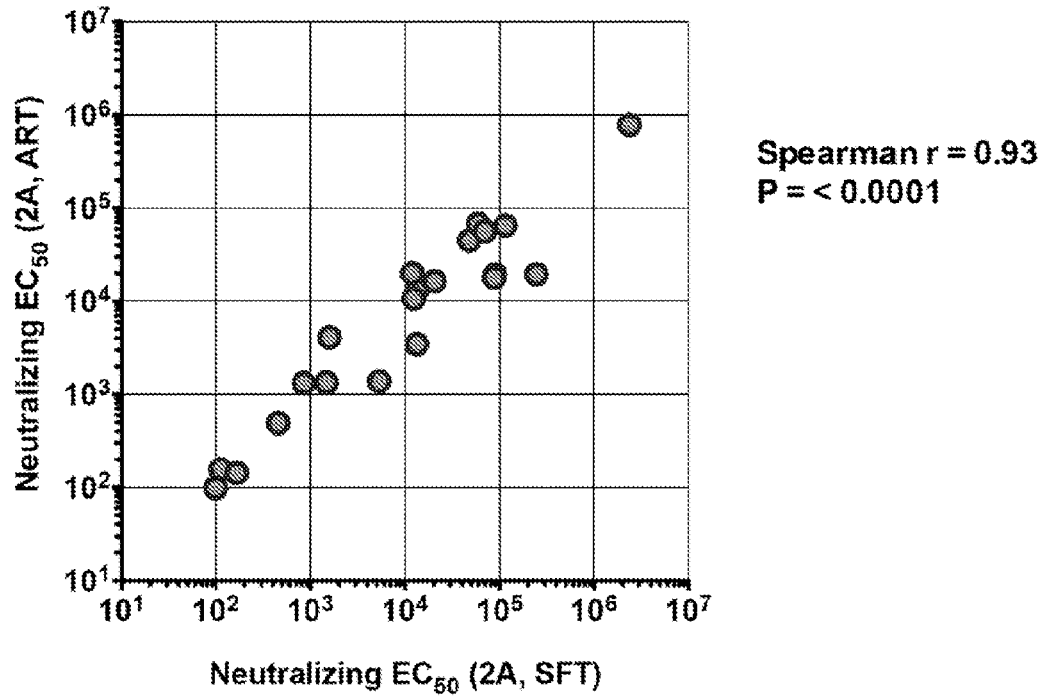
FIGS. 2A and 2B are a pair of graphs showing neutralizing titers for a panel of 24 anonymized serum samples from healthy human subjects.
Figure 2B:
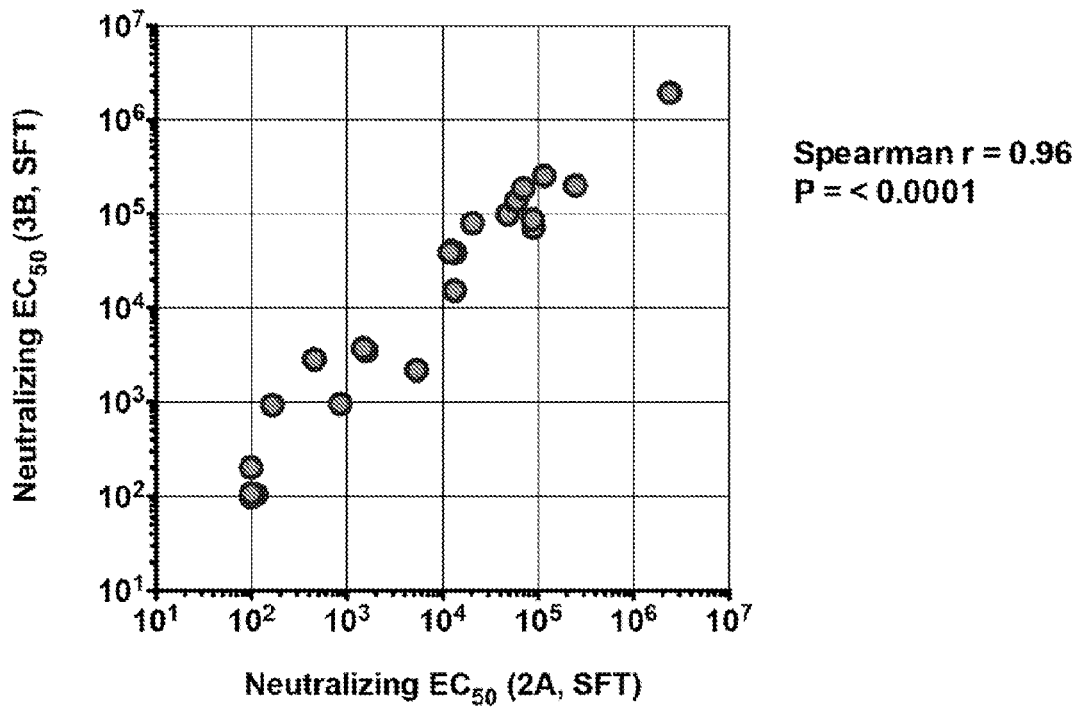

FIGS. 5A-5D is a series of panels showing neutralization of pseudovirus 5029m (FIG. 5A), 2A-269F (FIG. 5B), 5147m (FIG. 5C), and 5031mb (FIG. 5D) by sera from mice immunized with the indicated VLP immunogens after a priming dose and a booster dose four weeks later. Data are presented as $\log_{10} EC_{50}$ values.

FIG. 6 is a series of panels showing neutralization ($EC_{50}$) of wt (dark bars) or patient-cognate PML-mutant (light bars) pseudoviruses by sera from PML patients. (P) indicates patients whose disease progressed; (S) indicates patients who survived. Error bars represent standard error of the mean for data from three independent experimental replicates, two of which were performed with blinding. Arrows indicate date of onset of PML symptoms (date format is month/day/year).

FIG. 7 is a series of panels showing neutralization ($EC_{50}$) of the indicated pseudoviruses by sera from PML patients. (P) indicates patients whose disease progressed; (S) indicates patients who survived. Error bars represent standard error of the mean for data from three independent experimental replicates, two of which were performed with blinding. Arrows indicate date of onset of PML symptoms (date format is month/day/year).

FIG. 8 is a graph showing neutralizing titer against patient 5228's cognate PML-mutant JCV (squares) or inferred wt JCV (circles) during treatment and monitoring. Recombinant IL-7 (triangles) and JCV-1A VLPs (downward triangles) were administered at the indicated time points. Plasma JCV viral load ($\log_{10}$ copies/ml) is shown by small dots.

FIG. 9 is a graph showing neutralizing titer against patient 5228's cognate PML-mutant JCV (squares) or inferred wt JCV (circles) during treatment and monitoring (neutralization data are the same as shown in FIG. 8). CD4 T cell count is shown by diamonds.

FIGS. 10A-10C are a series of magnetic resonance imaging (MRI) images during the course of treatment showing evolution of PML lesions in patient 5228. Axial fluid-attenuated inversion recovery (FLAIR, FIG. 10A), diffusion-weighted imaging (DWI, FIG. 10B) and FLAIR-DWI merged images (FIG. 10C) show the evolution of PML lesions from July 2012 to March 2013. FIG. 10A shows a high signal intensity lesion of the right parieto-occipital white matter extending contralaterally through the corpus callosum; another focus is present in the left subcortical temporal region (July 2012). Subsequent examinations showed evolution of the signal alteration with progressive rapid extension of the lesions to the entire white matter bilaterally. In September 2012, the white matter was completely occupied by lesional and atrophic processes and enlargements of the ventricles and cortical sulci began to appear. The last examinations (January and March 2013) show progression of atrophy. FIG. 10B shows axial DWI images showing the evolution of the hyperintense signal alterations corresponding to the front of progression of PML lesions (white arrows). The signal alteration is substantially reduced starting from November 2012 and is no longer visible at the March 2013 examination, implying lesion stabilization. FIG. 10C shows merged FLAIR and DWI sequences showing the initial fronts of advance of PML lesions (black arrows), and their regression over time.

SEQUENCE LISTING

Any nucleic acid and amino acid sequences listed herein or in the accompanying sequence listing are shown using standard letter abbreviations for nucleotide bases and amino acids, as defined in 37 C.F.R. §1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Jun. 16, 2016, and is 66,057 bytes, which is incorporated by reference herein.

SEQ ID NO: 1 is the amino acid sequence of an exemplary JCV genotype 2A VP1 polypeptide.

SEQ ID NO: 2 is the amino acid sequence of an exemplary JCV genotype 3B VP1 polypeptide.

SEQ ID NO: 3 is the amino acid sequence of an exemplary JCV genotype 3B VP1 polypeptide with L55F mutation (55F).

SEQ ID NO: 4 is the amino acid sequence of an exemplary JCV genotype 3B VP1 polypeptide with L55F and N265S mutations (265S).

SEQ ID NO: 5 is the amino acid sequence of an exemplary JCV genotype 2A VP1 polypeptide with S267F and Q271H mutations (267F).

SEQ ID NO: 6 is the amino acid sequence of an exemplary JCV genotype 3B VP1 polypeptide with S267F and Q271H mutations (267F3B).

SEQ ID NO: 7 is the amino acid sequence of an exemplary JCV genotype 2A VP1 polypeptide with S269F mutation (269F).

SEQ ID NO: 8 is the amino acid sequence of an exemplary JCV genotype 3B VP1 polypeptide with L55F and Q271K mutations (271K).

SEQ ID NO: 9 is the amino acid sequence of an exemplary truncated JCV genotype 2 VP1 polypeptide (Y346* (GCN1)).

SEQ ID NO: 10 is the amino acid sequence of an exemplary JCV genotype 1A VP1 polypeptide.

SEQ ID NO: 11 is the amino acid sequence of an exemplary JCV genotype 1B VP1 polypeptide.

SEQ ID NO: 12 is the amino acid sequence of an exemplary JCV genotype 4 VP1 polypeptide.

SEQ ID NO: 13 is the amino acid sequence of an exemplary JCV genotype 6 VP1 polypeptide.

SEQ ID NO: 14 is the amino acid sequence of an exemplary JCV genotype 7 VP1 polypeptide.

SEQ ID NO: 15 is the amino acid sequence of an exemplary JCV genotype 8 VP1 polypeptide.

SEQ ID NO: 16 is a nucleic acid sequence encoding an exemplary JCV genotype 2B VP1 polypeptide.

SEQ ID NO: 17 is a nucleic acid sequence encoding an exemplary JCV genotype 3A VP1 polypeptide.

SEQ ID NO: 18 is a nucleic acid sequence encoding an exemplary truncated JCV genotype 2B VP1 polypeptide (Y346*(GCN1)).

SEQ ID NO: 19 is a nucleic acid sequence encoding an exemplary JCV genotype 1A VP1 polypeptide.

SEQ ID NO: 20 is a nucleic acid sequence encoding an exemplary JCV genotype 1B VP1 polypeptide.

SEQ ID NO: 21 is a nucleic acid sequence encoding an exemplary JCV genotype 4 VP1 polypeptide.

SEQ ID NO: 22 is a nucleic acid sequence encoding an exemplary JCV genotype 5 VP1 polypeptide.

SEQ ID NO: 23 is a nucleic acid sequence encoding an exemplary JCV genotype 7 VP1 polypeptide.

SEQ ID NO: 24 is a nucleic acid sequence encoding an exemplary JCV genotype 8 VP1 polypeptide.

SEQ ID NO: 25 is an exemplary codon-optimized nucleic acid sequence encoding a JCV genotype 2A VP1 polypeptide.

SEQ ID NO: 26 is an exemplary codon-optimized nucleic acid sequence encoding a JCV genotype 3B VP1 polypeptide.

SEQ ID NO: 27 is the amino acid sequence of an exemplary JCV genotype 1 Mad1 VP1 polypeptide.

DETAILED DESCRIPTION

Modern monoclonal antibody-based immunosuppressive therapeutics have been remarkably effective for treatment of a variety of diseases, ranging from cancer to various autoimmune conditions (Murad et al., *Curr. Mol. Med.* 13:165-178, 2013). Unfortunately, the therapeutic utility of many new immunosuppressive therapies is counterbalanced by rare but very serious JCV-induced PML side effects. In a specific example, multiple sclerosis patients who are both JCV seropositive in ELISA assays must weigh the strong likelihood that the drug natalizumab will effectively alleviate multiple sclerosis symptoms against the roughly 1% risk of developing PML during the first two years of therapy (Diotti et al., *Clin. Dev. Immunol.* 2013:967581, 2013).

Although the lethality of PML in HIV-infected individuals has declined dramatically with the advent of HAART, the disease continues to present a significant risk for HIV-infected individuals, with PML sometimes constituting the patient's first indication of HIV infection or first indication that HAART has not been fully effective (Simpson, *Cleveland Clin. J. Med.* 78:S24-27, 2011). At present, there are no significantly effective antiviral agents for treatment of JCV disease, and withdrawal of immunosuppression or HAART-induced reconstitution of immune function remain the only clinical approaches for treatment of PML. Unfortunately, the CNS damage caused by PML tends to be irreversible, and available therapeutic approaches can lead to immune reconstitution inflammatory syndrome, which is often lethal (Fox, *Cleveland Clin. J. Med.* 78:S33-37, 2011).

A stereotypical set of mutations have been identified in the JCV major capsid protein VP1 in viral isolates found in the cerebrospinal fluid (CSF) of PML patients (Gorelik et al., *J. Infect. Dis.* 204:103-114, 2011; Reid et al., *J. Infect. Dis.* 204:237-244, 2011). These PML-associated VP1 mutations are not found in WT JCV strains typically found in the urine. Based on the previous reports, WT JCV strains can be defined as having the following residues: 55L, 61S, 66D, 122H, 123S, 265N, 267S, 269S, and 271Q. As previously shown, various known PML-associated mutations typically occur in one or more of the listed residues; for example, the two most common PML-associated mutations are L55F and S269F (Gorelik et al., *J. Infect. Dis.* 204:103-114, 2011; Reid et al., *J. Infect. Dis.* 204:237-244, 2011).

The inventors have developed the first high-throughput system for quantitative analysis of JCV-neutralizing antibodies, described herein. Using this system, the inventors found that, as expected, most healthy sera contain antibodies capable of neutralizing WT JCV genotypes (for example, JCV genotype 2, such as JCV genotype 2A). Surprisingly, a minority of JCV genotype 2-neutralizing sera failed to neutralize one or more PML-associated VP1 mutant JCVs. These individuals may have a very limited diversity of functionally neutralizing serum antibodies, such that individual PML-associated point mutations in VP1 allow the virus to escape the binding of all effectively neutralizing antibodies. In this model, mutations in JCV VP1 that arise during the early stages of PML development may allow the virus to occupy a neutralization "blind spot" in some subjects' serum antibody repertoires. Such neutralization-escape mutations could increase the fitness of the virus, particularly in cases where T cell-mediated suppression of JCV replication in the CNS is impaired and antibody-mediated neutralization may therefore serve as a last line of defense against a spreading JCV infection.

The inventors' experimental VLP vaccination of mice described herein unexpectedly demonstrates that broadly cross-neutralizing antibody responses (including neutralization of JCV with variant VP1 polypeptides) could be elicited with VLPs representing a single WT JCV genotype. Also unexpectedly, VLPs representing PML-associated VP1 polypeptide mutants were less effective immunogens than WT-based compositions. This contrasts with findings reported for the related BK polyomavirus (BKV), wherein the achievement of high-titer broadly cross-neutralizing responses in mice required administration of a multivalent VLP inoculum representing multiple BKV genotypes (Pastrana et al., *J. Virol.* 87:10105-10113, 2013). The neutralizing responses elicited in mice with a single WT JCV VP1 polypeptide were effective against JCV with either WT or PML-associated mutant VP1 polypeptides (Example 3). Similar results were obtained in rabbit immunization studies (Example 4). These discoveries suggest that it is not necessary to vaccinate individuals with a spectrum of VP1 polypeptides from different JCV genotypes and it is also unnecessary to vaccinate with VP1 polypeptides representing PML-associated mutants to achieve effective broadly cross-neutralizing antibody responses. In fact, the existing dataset indicates that it appears to be preferable to immunize using the VP1 of WT JCV genotypes, since these tend to give higher, more broadly cross-neutralizing antibody responses. The idea that it is not necessary to vaccinate individuals using a mixture of VLPs representing different PML-mutant JCV VP1 polypeptides is important, given the large number of different VP1 variant polypeptides that have been identified in individuals who develop PML (Gorelik et al., *J. Infect. Dis.* 204:103-114, 2011; Reid et al., *J. Infect. Dis.* 204:237-244, 2011).

A recent report by Maginnis and colleagues reported that JCV pseudoviruses and native viruses based on various PML-associated VP1 mutations were non-infectious on all tested cell lines (Maginnis et al., *mBio* 4:e00247-13, 2013). However, as demonstrated herein, PML-associated mutants are competent for infectious entry into a limited spectrum of previously untested cell types. A possible model for this finding is that previously tested cell lines may lack an infectious entry factor, such as an alternative receptor, that PML mutant genotypes require for infectious entry. The identification of cell lines permissive for entry of PML-associated JCV mutants is useful for experiments investigating JCV entry tropism, for performing functional neutralization serology, and for exploration of possible implications for the etiology of PML.

I. Abbreviations

CNS central nervous system
CSF cerebrospinal fluid
HAART highly active antiretroviral therapy
HIV human immunodeficiency virus
JCV JC polyomavirus
PML progressive multifocal leukoencephalopathy
RLU relative light units
VLP virus-like particle
VP1 viral protein 1
WT wild type II. Terms Unless otherwise noted, technical terms are used according to conventional usage. Definitions of common terms in molecular biology may be found in *Lewin's Genes X*, ed. Krebs et al, Jones and Bartlett Publishers, 20009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics,* 3rd Edition, Springer, 2008 (ISBN: 1402067534).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a polypeptide" includes single or plural polypeptides and is considered equivalent to the phrase "comprising at least one polypeptide." As used herein, "comprises" means "includes." Thus, "comprising A or B," means "including A, B, or A and B," without excluding additional elements.

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Adjuvant: An agent that increases an immunogenic response to an antigen. Adjuvants are inorganic or organic compounds or mixtures of compounds. Exemplary adjuvants include aluminum salts or gels (such as aluminum hydroxide or aluminum phosphate), oil-in-water or water-in-oil emulsions, and ligands for pattern recognition receptors (PRR) (such as ligands for Toll-like receptors (TLRs), NOD-like receptors (NLRs), RIG-I-like receptors (RLRs) and C-type lectin receptors (CLRs)). Cytokines or growth factors may also be used as adjuvants. In some examples, an immunogenic composition includes an adjuvant.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A neutralizing antibody is an antibody which, on mixture with the homologous infectious agent (such as JCV), reduces the infectious titer. In some examples, a neutralizing antibody is an antibody that blocks the ability of its antigen to perform a physiological function. Assays to detect neutralizing antibodies include but are not limited to those described herein.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antigen: A molecule that stimulates an immune response. Antigens are usually proteins or polysaccharides or fragments thereof. An epitope is an antigenic determinant. These are particular chemical groups or peptide sequences on a molecule that are antigenic, such that they elicit a specific immune response. An antibody binds a particular antigenic epitope.

Consists essentially of: With respect to an immunogenic composition, an immunogenic composition consists essentially of a specified antigen (such as a JCV VP1 polypeptide or a nucleic acid encoding the polypeptide) if it does not include any additional antigens. However, the immunogenic composition can include additional non-antigen components, such as pharmaceutically acceptable carriers, adjuvants, preservatives, or the like.

With regard to a polypeptide, a polypeptide consists essentially of a specified amino acid sequence if it does not include any additional amino acid residues. However, the polypeptide can include additional non-peptide components, such as labels (for example, fluorescent, radioactive, or solid particle labels), sugars or lipids. With regard to a nucleic acid molecule, a nucleic acid molecule consists essentially of a specified nucleotide sequence if it does not include any additional nucleotides. However, the nucleic acid molecule can include additional non-nucleotide components, such as labels (for example, fluorescent, radioactive, or solid particle labels), sugars or lipids.

Effective amount: A quantity of a specified agent sufficient to achieve a desired effect. For example, an effective amount (such as a therapeutically effective amount) may be the amount of a JCV VP1 polypeptide or nucleic acid (or fragment thereof) useful for eliciting an immune response against JCV in a subject and/or for inhibiting or preventing infection or pathology by JCV in a subject. Ideally, in the context of the present disclosure, an effective amount of a JCV VP1 polypeptide or nucleic acid (or fragment thereof) is an amount sufficient to elicit an immune response to JCV and/or increase resistance to, prevent, ameliorate, and/or treat infection caused by JCV in a subject without causing a substantial cytotoxic effect in the subject. The effective amount of a JCV polypeptide or nucleic acid (or fragment thereof) useful for eliciting an immune response to JCV and/or increasing resistance to, preventing, ameliorating, and/or treating JCV infection or pathology in a subject will be dependent on, for example, the subject being treated, the manner of administration of the composition, and other factors.

Epitope: An antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Immune response: A response of a cell of the immune system, such as a B-cell, T-cell, macrophage or polymorphonucleocyte, to a stimulus such as an antigen. An immune response can include any cell of the body involved in a host defense response, for example, an epithelial cell that secretes an interferon or a cytokine. An immune response includes, but is not limited to, an innate immune response or inflammation.

Immunocompromised: An immunocompromised subject is a subject who is incapable of developing or unlikely to develop a robust immune response, usually as a result of disease, malnutrition, or immunosuppressive therapy. An immunocompromised immune system is an immune system that is functioning below normal. Immunocompromised subjects are more susceptible to opportunistic infections, for example viral, fungal, protozoan, or bacterial infections, prion diseases, and certain neoplasms.

Those who can be considered to be immunocompromised include, but are not limited to, subjects with AIDS (or HIV positive), subjects with severe combined immunodeficiency, diabetics, subjects who have had transplants and who are taking immunosuppressants, and those who are receiving chemotherapy for cancer. Immunocompromised individuals also include subjects with most forms of cancer (other than skin cancer), sickle cell anemia, cystic fibrosis, those who do not have a spleen, subjects with end stage kidney disease (dialysis), and those who have been taking corticosteroids or other immune suppressing therapy on a frequent basis within the last year.

Immunogenic Composition: A composition useful for stimulating or eliciting a specific immune response (or immunogenic response) in a subject. In some embodiments, the immune response is protective or provides protective immunity, in that it enables the subject to better resist infection or disease progression that results from infection with the organism against which the immunogenic composition is directed. In particular examples, an immunogenic composition includes a pharmaceutically acceptable carrier and/or an adjuvant. One specific type of an immunogenic composition is a vaccine.

An immunogenic composition may be a monovalent immunogenic composition, which contains a single antigen (such as a single polypeptide or fragment thereof, or a nucleic acid encoding a single polypeptide or fragment thereof) or two or more antigens from a single organism or a single subtype or genotype of an organism. An immunogenic composition may also be a multivalent (or polyvalent) immunogenic composition which contains antigens from two or more organisms or two or more subtypes or genotypes of a single organism.

Immunosuppressant: Any compound that decreases the function or activity of one or more aspects of the immune system, such as a component of the humoral or cellular immune system or the complement system. Immunosuppressants are also referred to as "immunosuppressive agents" or "immunosuppressive therapies."

In some examples, an immunosuppressant includes, but is not limited to: (1) antimetabolites, such as purine synthesis inhibitors (such as inosine monophosphate dehydrogenase (IMPDH) inhibitors, e.g., azathioprine, mycophenolate, and mycophenolate mofetil), pyrimidine synthesis inhibitors (e.g., leflunomide and teriflunomide), and antifolates (e.g., methotrexate); (2) calcineurin inhibitors, such as tacrolimus, cyclosporine A, pimecrolimus, and voclosporin; (3) TNF-α inhibitors, such as thalidomide and lenalidomide; (4) IL-1 receptor antagonists, such as anakinra; (5) mammalian target of rapamycin (mTOR) inhibitors, such as rapamycin (sirolimus), deforolimus, everolimus, temsirolimus, zotarolimus, and biolimus A9; (6) corticosteroids, such as prednisone; and (7) antibodies to any one of a number of cellular or serum targets (including anti-lymphocyte globulin and anti-thymocyte globulin).

Exemplary cellular targets and their respective inhibitor compounds include, but are not limited to complement component 5 (e.g., eculizumab); tumor necrosis factors (TNFs) (e.g., infliximab, adalimumab, certolizumab pegol, afelimomab and golimumab); IL-5 (e.g., mepolizumab); IgE (e.g., omalizumab); BAYX (e.g., nerelimomab); interferon (e.g., faralimomab); IL-6 (e.g., elsilimomab); IL-12 and IL-13 (e.g., lebrikizumab and ustekinumab); CD3 (e.g., muromonab-CD3, otelixizumab, teplizumab, visilizumab); CD4 (e.g., clenoliximab, keliximab and zanolimumab); CD11a (e.g., efalizumab); CD18 (e.g., erlizumab); CD20 (e.g., rituximab, afutuzumab, ocrelizumab, pascolizumab); CD23 (e.g., lumiliximab); CD40 (e.g., teneliximab, toralizumab); CD52 (e.g., alemtuzumab); CD62L/L-selectin (e.g., aselizumab); CD80 (e.g., galiximab); CD147/basigin (e.g., gavilimomab); CD154 (e.g., ruplizumab); BLyS (e.g., belimumab); CTLA-4 (e.g., ipilimumab, tremelimumab); CAT (e.g., bertilimumab, lerdelimumab, metelimumab); integrin (e.g., natalizumab); IL-6 receptor (e.g., tocilizumab); LFA-1 (e.g., odulimomab); and IL-2 receptor/CD25 (e.g., basiliximab, daclizumab, inolimomab).

Inhibiting or treating a disease: "Inhibiting" a disease refers to inhibiting the full development of a disease (for example, PML). Inhibition of a disease can span the spectrum from partial inhibition to substantially complete inhibition (e.g., including, but not limited to prevention) of the disease. In some examples, the term "inhibiting" refers to reducing or delaying the onset or progression of a disease. A subject to be administered an effective amount of the disclosed immunogenic compositions can be identified by standard diagnosing techniques for such a disorder, for example, basis of family history, or risk factors to develop the disease or disorder (such as being immunocompromised). "Treatment" refers to a therapeutic intervention that ameliorates a sign or symptom of a disease or pathological condition (such as PML) after it has begun to develop.

Isolated: An "isolated" or "purified" biological component (such as a nucleic acid, peptide, protein, protein complex, or virus-like particle) has been substantially separated, produced apart from, or purified away from other biological components in the cell of the organism in which the component occurs, for example, other chromosomal and extrachromosomal DNA and RNA, and/or proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins.

The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

JC polyomavirus (JCV): A polyomavirus originally isolated from a patient (J.C.) with progressive multifocal leukoencephalopathy (Padgett et al., *Lancet* 1:1257-1260, 1971). JCV is genetically similar to BKV and simian virus 40 (SV40). JCV is very common in the general population, with a majority of individuals seropositive for JCV. The initial site of infection may be the tonsils or gastrointestinal tract. The primary sites of JC infection are thought to be tubular epithelial cells in the kidney, the lining of the ureters and bladder, and oligodendrocytes and astrocytes in the central nervous system.

JCV isolates have been classified into distinct genotypes or subtypes, based in part on the amino acid sequences of VP1 proteins of individual isolates (Cubitt et al., *J. Neurovirol.* 7:339-344, 2001; Agostini et al., *J. Gen. Virol.* 82:1221-1331, 2001). As used herein, the term "genotype" refers to the classical JCV subtypes (e.g., genotypes 1, 2, 3, 4, 5, 6, 7, or 8) or to JCV having a variation or mutation compared to a WT JCV sequence, including PML-associated JCV having one or more mutations in a VP1 nucleic acid and/or amino acid sequence.

JCV can reactivate in immunocompromised individuals and can cause JCV-associated progressive multifocal leukoencephalopathy (PML), which is frequently fatal or causes irreversible CNS damage. PML occurs in about 1-3% of patients suffering from HIV-induced AIDS and can also occur in other immunosuppressed patients, including but not limited to patients treated with rituximab, natalizumab, alemtuzumab, or efalizumab. JCV can also cause urinary tract pathology in some organ transplant recipients.

GenBank Accession Nos. NC_001699, AB038251, and AF281600 disclose exemplary JCV nucleic acid sequences, all of which are incorporated by reference as present in GenBank on Nov. 26, 2013. VP1 polypeptide sequences are also publicly available.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more immunogenic compositions, such as one or more JCV VP1 polypeptides or nucleic acids or fragments thereof, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polyomavirus: A family of viruses having a non-enveloped icosahedral capsid. The approximately 5 kb circular DNA genome of polyomaviruses encodes non-structural proteins (large T-antigen and small t-antigen) and structural proteins (VP1, VP2, and VP3), and also includes a non-coding region including an origin of replication and promoters. Polyomaviruses include but are not limited to BK polyomavirus, JC polyomavirus, Merkel cell polyomavirus, and simian virus 40 (SV40). Related human polyomaviruses WU virus (Gaynor et al., *PLoS Pathog.* 3:e64, 2007) and KI virus (Allander et al., *J. Virol.* 81:4130-4136, 2007) have recently been reported in clinical samples. There are currently a total of 12 known human polyomaviruses (see, e.g., Ehlers and Wieland, *APMIS* 121:783-795, 2013).

Sample or biological sample: A biological specimen containing DNA, RNA (including mRNA), protein, or combinations thereof, obtained from a subject. Examples include, but are not limited to, peripheral blood, serum, urine, saliva, tissue biopsy, fine needle aspirate, surgical specimen, and autopsy material. In particular examples, a sample includes a blood sample or a serum sample.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman, *Adv. Appl. Math.* 2: 482, 1981; Needleman & Wunsch, *J. Mol. Biol.* 48: 443, 1970; Pearson & Lipman, *Proc. Natl. Acad. Sci.* USA 85: 2444, 1988; Higgins & Sharp, *Gene,* 73: 237-244, 1988; Higgins & Sharp, *Comput. Appl. Biosci.* 5: 151-153, 1989; Corpet et al., *Nucl. Acids Res.* 16, 10881-90, 1988; Huang et al., *Comput. Appl. Biosci.* 8, 155-65, 1992; and Pearson, *Methods Mol. Biol.* 24:307-331, 1994. Altschul et al. (*J. Mol. Biol.* 215:403-410, 1990) presents a detailed consideration of sequence alignment methods and homology calculations.

The NCBI Basic Local Alignment Search Tool (BLAST) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Subject: Living multi-cellular vertebrate organisms, a category that includes both human and non-human mammals (such as mice, rats, rabbits, sheep, horses, cows, and non-human primates).

Vaccine: A composition (such as an immunogenic composition) that elicits a prophylactic or therapeutic immune response in a subject. In some cases, the immune response is a protective response. Typically, a vaccine elicits an antigen-specific immune response to an antigen of a pathogen, for example, a bacterial or viral pathogen, or to a cellular constituent correlated with a pathological condition. A vaccine may include a polynucleotide, a peptide or polypeptide, a VLP, a polysaccharide, a virus, a bacterium, a cell or one or more cellular constituents.

Virus-like particle (VLP): A non-replicating viral shell, derived from any of several viruses, such as polyomaviruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) *Biophys. J.* 60:1445-1456; Hagensee et al. (1994) *J. Virol.* 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

VP1 polypeptide: One of three capsid proteins that make up the outer protein coat of viruses. VP1 is the major capsid protein of polyomaviruses, such as JCV. The VP1 polypeptide interacts with a target cell to provide virion attachment to the target cell. Exemplary JCV VP1 amino acid sequences are publicly available and include GenBank Accession Nos. AAK97910 (type 2A; SEQ ID NO: 1) and AAG34667 (type 3B; SEQ ID NO: 2), each of which is incorporated herein by reference as present in GenBank on Nov. 26, 2013. Additional VP1 polypeptide amino acid and nucleic acid sequences are publicly available.

III. Methods of Eliciting an Immune Response to JCV

Disclosed herein are methods of eliciting an immune response to JCV. In some embodiments, the methods elicit a neutralizing immune response to JCV, such as neutralizing antibodies. In particular examples, the methods elicit a neutralizing response to one or more WT JCV genotypes or subtypes, such as one or more of JCV genotypes 1 (e.g., genotypes 1A or 1B), 2 (e.g., genotypes 2A, 2B, or 2C), 3 (e.g., genotypes 3A or 3B), 4, 5, 6, 7 (e.g. genotypes 7A, 7B, or 7C), and 8 (e.g., genotypes 8A or 8B). In particular examples, the methods include eliciting an immune response (such as a neutralizing antibody response) to JCV genotypes with WT VP1 polypeptides and to JCV genotypes with variant (or mutant) VP1 polypeptides. In some examples, variant JCV VP1 polypeptides include those with substitutions at one or more VP1 amino acid positions (wild type amino acids listed) 55L, 61S, 66D, 122H, 123S, 265N, 267S, 269S, or 271Q compared to WT JCV VP1 (see e.g., WO 2010/090757). One of skill in the art can identify additional variant JCV VP1 polypeptides, for example by sequencing JCV isolates from patients with PML.

In some embodiments, the methods include eliciting an immune response against JCV (such as a neutralizing antibody response) in a subject. The methods include administering to a subject an effective amount of an immunogenic composition including an isolated JCV VP1 polypeptide or a fragment thereof (such as at least one JCV genotype 1A, 1B, 2A, 2B, 2C, 3A, 3B, 4, 5, 6, 7A, 7B, 7C, 8A, or 8B VP1 polypeptide), or a nucleic acid encoding the JCV VP1 polypeptide, such as those disclosed below. In some examples, the subject does not have detectable JCV neutralizing antibodies (such as JCV serum antibodies capable of neutralizing PML-associated JCV VP1 mutant polypeptide genotypes, such as L55F or S269F VP1 mutant polypeptides).

In particular examples, the methods include administering to a subject an effective amount of an immunogenic composition including an isolated JCV genotype 2 VP1 polypeptide (such as a JCV genotype 2A VP1 polypeptide), an isolated JCV genotype 3 VP1 polypeptide (such as a JCV genotype 3B VP1 polypeptide), or a combination thereof. In other examples, the methods include administering to a subject an effective amount of an immunogenic composition including one or more isolated WT JCV VP1 polypeptides (such as one or more WT JCV genotype 1A, 1B, 2A, 2B, 2C, 3A, 3B, 4, 5, 6, 7A, 7B, 7C, 8A, or 8B VP1 polypeptides; for example, polypeptides with at least 98% or 99% identity to one or more of SEQ ID NOs: 1, 2, 9-15, and 27). In some examples, the methods include administering to a subject an effective amount of an immunogenic composition including a WT JCV genotype 2 VP1 polypeptide (for example WT JCV genotype 2A VP1), an isolated WT JCV genotype 3 VP1 polypeptide (for example WT JCV genotype 3B VP1), an isolated WT JCV genotype 1 VP1 polypeptide (for example WT JCV genotype 1A VP1), or a combination thereof, thereby eliciting an immune response to JCV in the subject. In particular methods, the WT JCV VP1 polypeptide(s) elicits a neutralizing antibody response to one or more JCV VP1 variant polypeptides.

In particular examples, administering the JCV VP1 polypeptide includes administering a VLP including one or more JCV VP1 polypeptides. In additional examples, the methods include administering to a subject an immunogenic composition including one or more JCV VP1 polypeptides assembled into a pentameric capsomer or other disassembled non-VLP structures.

In other examples, the methods include administering to a subject an effective amount of an immunogenic composition including an isolated nucleic acid encoding a JCV VP1 polypeptide (for example, nucleic acids with at least 90% identity to one or more of SEQ ID NOs: 16-26). In particular examples, the methods include administering to a subject an effective amount of an immunogenic composition including an isolated nucleic acid encoding genotype 2A VP1 polypeptide and/or an isolated nucleic acid encoding a JCV genotype 3B VP1 polypeptide.

In some embodiments, the methods disclosed herein include administering to the subject an immunogenic composition that consists essentially of an isolated JCV VP1 polypeptide or a combination of JCV VP1 polypeptides, or an isolated nucleic acid encoding the VP1 polypeptide(s). In some examples, the immunogenic composition consists essentially of a single isolated WT JCV VP1 polypeptide (for example, a polypeptide with at least 98% or 99% identity to one of SEQ ID NOs: 1, 2, 9-15, or 27) or a nucleic acid encoding the VP1 polypeptide (for example, a nucleic acid with at least 90% identity to one of SEQ ID NOs: 16-26). In particular examples, the immunogenic composition includes an isolated WT JCV genotype 2 VP1 polypeptide (such as a JCV genotype 2A VP1 polypeptide, for example, a polypeptide with at least 99% identity to SEQ ID NO: 1 or 9), an isolated WT JCV genotype 3 VP polypeptide (such as a JCV genotype 3B VP1 polypeptide, for example, a polypeptide with at least 99% identity to SEQ ID NO: 2), an isolated WT JCV genotype 1 VP polypeptide (such as a JCV genotype 1A VP1 polypeptide, for example, a polypeptide with at least 99% identity to SEQ ID NO: 10 or SEQ ID NO: 27), or a nucleic acid encoding the polypeptide. An immunogenic composition that consists essentially of a JCV genotype 2 VP1 polypeptide does not include any other JCV antigens (for example, does not include any other JCV polypeptides), but may include additional non-antigen components, including but not limited to pharmaceutically acceptable carriers, adjuvants, wetting agents, emulsifiers, and so on. Similarly, an immunogenic composition that consists essentially of a JCV genotype 3 VP1 polypeptide does not include any other JCV antigens (for example, does not include any other JCV polypeptides), but may include additional non-antigen components, including but not limited to pharmaceutically acceptable carriers, adjuvants, wetting agents, emulsifiers, and so on. An immunogenic composition that consists essentially of a JCV genotype 2 VP1 polypeptide and a JCV genotype 3 VP1 polypeptide does not include any other JCV antigens (for example, does not include any other JCV polypeptides), but may include additional non-antigen components, including but not limited to pharmaceutically acceptable carriers, adjuvants, wetting agents, emulsifiers, and so on.

In other embodiments, the methods disclosed herein include administering to the subject a monovalent immunogenic composition that includes an isolated WT JCV VP1 polypeptide (for example, a WT genotype 2A, 3B, or 1A VP1 polypeptide) or an isolated nucleic acid encoding the VP1 polypeptide. In one example, a monovalent JCV genotype 2 VP1 polypeptide immunogenic composition is an immunogenic composition that does not include any polypeptides from any other virus (such as other JCV genotypes), though it may include additional JCV genotype 2 polypeptides, such as JCV genotype 2 VP2 and/or VP3 polypeptides. Similarly, in another example, a monovalent JCV genotype 3 VP1 polypeptide immunogenic composition is an immunogenic composition that does not include any polypeptides from any other virus (such as other JCV genotypes), though it may include additional JCV genotype 3 polypeptides, such as JCV genotype 3 VP2 and/or VP3 polypeptides. Polypeptides from particular JCV genotypes can be identified by analysis of their amino acid sequences (see, e.g., Cubitt et al., *J. NeuroVirol.* 7:339-344, 2001; Agostini et al., *J. Gen. Virol.* 82:1221-1331, 2001).

In some embodiments, the methods further include selecting a subject in need of enhanced immunity to JCV. In some examples, a subject in need of enhanced immunity to JCV is a subject at risk of JCV infection or at risk of developing JCV-associated disorders, such as PML or other diseases of the central nervous system (including, but not limited to stroke, brain tumors, or dementia, for example Alzheimer disease). Subjects in need of enhanced immunity to JCV include subjects who are immunocompromised, for example subjects who are infected with human immunodeficiency virus (HIV), subjects with severe combined immunodeficiency, subjects with idiopathic CD4 lymphopenia, pregnant women, diabetics, subjects who are receiving chemotherapy for cancer, subjects who are receiving or are candidates for immunosuppressive therapy (such as corticosteroids, a calcineurin inhibitor, such as tacrolimus, cyclosporine, or pimecrolimus, or other therapies that decrease immune system function, such as rituximab, natalizumab, efalizumab, or alemtuzumab), and elderly subjects (for example, human subjects 65 years of age or older). In some examples, subjects who are receiving immunosuppressive therapy include individuals who have received or are a candidate for an organ transplant (such as a renal transplant or other solid organ transplant or a bone marrow transplant). In one example, a subject in need of enhanced immunity to JCV is a renal transplant recipient or a bone marrow transplant recipient. In another example, a subject in need of enhanced immunity to JCV is a subject who is receiving an immunosuppressive therapy which is known to increase risk of PML, such as rituximab, natalizumab, alemtuzumab, or efalizumab therapy (or a subject who will or has received such therapy). In a further example, a subject in need of enhanced immunity to JCV is a subject diagnosed with PML.

IV. JCV VP1 Polypeptides

JCV nucleic acid and protein sequences are publicly available and include, but are not limited to GenBank Accession Nos. NC_001699, AF300945, and AY536541, each of which is incorporated herein by reference as present in GenBank on Dec. 11, 2013.

It is disclosed herein that several JCV VP1 polypeptides (or fragments thereof) can be used to elicit an immune response to JCV, for example, an immune response capable of neutralizing multiple JCV genotypes. In some examples, JCV polypeptides comprise, consist essentially of, or consist of the amino acid sequences set forth as SEQ ID NOs: 1-15 and 27. The genotype of each amino acid sequence is indicated in Table 1.

TABLE 1

Genotypes of exemplary JCV VP1 polypeptides

| Genotype | SEQ ID NO: |
|---|---|
| 2A | 1 |
| 3B | 2 |
| 3B L55F | 3 |
| 3B L55F, N265S | 4 |
| 2A S267F, Q271H | 5 |
| 3B S267F, Q271H | 6 |
| 2A S269F | 7 |
| 3B L55F, Q271K | 8 |
| 2A Y346* (GCN) | 9 |
| 1A | 10 |
| 1B | 11 |
| 4 | 12 |
| 6 | 13 |
| 7 | 14 |
| 8 | 15 |
| Mad 1 (1A) | 27 |

Additional exemplary JCV genotype 2 VP1 polypeptides include GenBank Accession Nos. AAC40846, AAK97910 (SEQ ID NO: 1), AAK97964, BAC15641, BAB68797, AAM89327, AAC59478, AAC59484, AAC59502, AAC59514, AAC59520, and AAC59490, each of which is incorporated herein by reference as present in GenBank on Dec. 11, 2013. Additional exemplary JCV genotype 3 VP1 polypeptides include GenBank Accession Nos. AAB41717, AAG34667 (SEQ ID NO: 2), AAR89211, BAE02956, AAT09837, AAR89271, and AAB41711, each of which is incorporated by reference as present in GenBank on Dec. 11, 2013. One of ordinary skill in the art can identify additional JCV VP1 polypeptides, for example, based on sequence comparison to the amino acid sequences provided herein.

In some embodiments, the JCV VP1 polypeptides of use in the methods disclosed herein have a sequence at least 98%, 99%, or 100% identical to the amino acid sequence set forth in one of SEQ ID NOs: 1-15 and 27. Minor modifications of JCV VP1 polypeptide primary amino acid sequences may result in peptides that have substantially equivalent activity as compared to the unmodified counterpart polypeptide described herein. Such modifications may be deliberate, as by site-directed mutagenesis, or may be spontaneous. All of the polypeptides produced by these modifications are included herein. Thus, a specific, non-limiting example of a JCV VP1 polypeptide is a conservative variant of the JCV VP1 polypeptide (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). A table of conservative substitutions is provided herein (Table 2). Substitutions of the amino acids sequences shown in SEQ ID NOs: 1-15 and 27 can be made based on this table.

TABLE 2

Exemplary conservative amino acid substitutions

| Original Amino Acid | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In some examples the modifications of VP1 polypeptides are not at positions that distinguish between WT JCV genotypes. For example, JCV genotype 1 VP1 polypeptide (such as genotype 1A) in some examples may be distinguished from JCV genotype 2 VP1 polypeptide (such as genotype 2A) by amino acid differences at positions 117 (Ser), 158 (Leu), and 345 (Lys), and in some examples, also position 75 (Arg) (JCV 1A amino acids in parentheses). JCV genotype 2 (such as subtype 2A) VP1 polypeptide may be distinguished from JCV genotype 3 (such as subtype 3B) VP1 polypeptide at positions 134 (Ala), 164 (Thr), 321 (Ile), and 332, (Gln) (JCV 3B amino acids shown in parentheses). An alignment of exemplary JCV genotype 1 (1A), 2 (2A), and 3 (3B) VP1 polypeptides is shown in FIG. 1. Thus, in some examples, the JCV genotype 2 and 3 polypeptides do not include variations at these amino acids, though they may include one or more (such as 2, 3, 4, 5, or more) variations at other amino acid positions. In other examples, the VP1 polypeptides do not include amino acid substitutions at one or more positions identified in "variant" VP1 polypeptides, such as amino acid positions 55L, 61S, 66D, 122H, 123S, 265N, 267S, 269S, or 271Q (wild type amino acids listed; see, e.g., Gorelik et al., *J. Inf. Dis.* 204:103-114, 2011; Reid et al., *J. Inf. Dis.* 204:237-244, 2011).

An "epitope" or "antigenic determinant" refers to a site on an antigen to which B and/or T cells respond. T cells can respond to the epitope when the epitope is presented in conjunction with an MHC molecule. Epitopes can be formed both from contiguous amino acids (linear) or noncontiguous amino acids juxtaposed by tertiary folding of an antigenic polypeptide (conformational). Epitopes formed from contiguous amino acids are typically retained on exposure to denaturing solvents whereas epitopes formed by tertiary folding are typically lost on treatment with denaturing solvents. Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 5 and 15 amino acids, such as 5, 6, 7, 8, 9, 10, 11, 12, 13, 14, or 15 amino acids. In some examples, the immunogenic compositions disclosed herein include a fragment (such as an immunogenic fragment) or antigenic determinant of a JCV VP1 protein. One of skill in the art can identify predicted antigenic determinants, for example using an HLA peptide binding prediction program, such as BIMAS (www-bimas.cit.nih.gov/molbio/hla_bind/) or IEDB analysis resource (immuneeptiope.org). In some examples, the JCV VP1 polypeptide includes, consists essentially of, or consists of five or more amino acids (for example, 5, 6, 7, 8, 9, 10, 11, 12, 13, 14, 15, 16, 17, 18, 19, 20, 21, 22, 23, 24, 25, or more amino acids) of any one of the VP1 polypeptides set forth as SEQ ID NOs: 1-15 and 27. In other examples, the VP1 polypeptide includes, consists essentially of, or consists of five or more amino acids (for example, 5, 6, 7, 8, 9, 10, 11, 12, 13, 14, 15, 16, 17, 18, 19, 20, 21, 22, or 23 amino acids) of the VP1 BC loop (e.g., about amino acids 53-75 of a JCV VP1 polypeptide).

Polynucleotides encoding the JCV VP1 polypeptides disclosed herein are also provided. In some examples, JCV VP1 encoding polynucleotides comprise, consist essentially of, or consist of the nucleic acid sequences set forth as SEQ ID NOs: 16-24. The genotype of each nucleic acid sequence is indicated in Table 3.

TABLE 3

Genotypes of exemplary JCV VP1 nucleic acids

| Genotype | SEQ ID NO: |
|---|---|
| 2A | 16 |
| 3B | 17 |
| 2A Y346* (GCN) | 18 |
| 1A | 19 |
| 1B | 20 |
| 4 | 21 |
| 6 | 22 |
| 7 | 23 |
| 8 | 24 |

Additional exemplary JCV genotype 2A VP1 polypeptide encoding nucleic acid sequences include GenBank Accession Nos. AF030085 (nucleotides 1467-2531), AF300945 (nucleotides 1193-2257), AF300954 (nucleotides 1193-2257), AB081602 (nucleotides 1460-2524), AB048546 (nucleotides 1460-2524), AY121912 (nucleotides 1193-2257; SEQ ID NO: 16), AF015529 (nucleotides 1193-2257), AF015530 (nucleotides 1193-2257), and AF015331 (nucleotides 1193-2257), each of which is incorporated herein by reference as present in GenBank on Dec. 11, 2013. Additional exemplary JCV genotype 2B VP1 polypeptide encoding nucleic acid sequences include GenBank Accession No. AF015533 (nucleotides 1193-2257), which is incorporated by reference as present in GenBank on Dec. 11, 2013. Additional exemplary JCV genotype 2C VP1 polypeptide encoding nucleic acid sequences include GenBank Accession Nos. AF015535 (nucleotides 1193-2257) and AF015536 (nucleotides 1193-2257), both of which are incorporated by reference as present in GenBank on Dec. 11, 2013. Additional exemplary JCV genotype 3A VP1 polypeptide encoding nucleic acid sequences include GenBank Accession No. U73502 (nucleotides 1460-2524), which is incorporated by reference as present in GenBank on Dec. 11, 2013. Additional exemplary JCV genotype 3B VP1 polypeptide encoding nucleic acid sequences include GenBank Accession Nos. AF295731 (nucleotides 1193-2257; SEQ ID NO: 17), AY382184 (nucleotides 1193-2257), AB126992 (nucleotides 1460-2524), AY536242 (nucleotides 1428-2492), AY376829 (nucleotides 1193-2257), and U73501 (nucleotides 1460-2524), each of which is incorporated by reference as present in GenBank on Dec. 11, 2013. One of ordinary skill in the art can identify additional nucleic acid sequences encoding JCV VP1 polypeptides, for example based on sequence comparison to the nucleic acid sequences provided herein.

In some embodiments, the nucleic acid sequences encoding JCV VP1 polypeptides of use in the methods disclosed herein have a sequence at least 85%, 90%, 95%, 96%, 97%, 98%, or 99%, such as 100% identical to the nucleic acid sequence set forth in one of SEQ ID NOs: 16-24. In some embodiments, the nucleic acids encoding the JCV VP1 polypeptides are codon-optimized for expression in a heterologous system (such as mammalian cells, bacteria or yeast). Exemplary codon-optimized JCV VP1 encoding nucleic acids comprise, consist essentially of, or consist of SEQ ID NO: 25 (JCV genotype 2A) and SEQ ID NO: 26 (JCV genotype 3B).

The JCV VP1 polypeptides disclosed herein can be chemically synthesized by standard methods, or can be produced recombinantly. An exemplary process for polypeptide production is described in Lu et al., *FEBS Lett.* 429:31-35, 1998. They can also be isolated by methods including preparative chromatography and immunological separations. Polypeptides can also be produced using molecular genetic techniques, such as by inserting a nucleic acid encoding a JCV VP1 polypeptide or an epitope thereof into an expression vector, introducing the expression vector into a host cell, and isolating the polypeptide. Any suitable cell can be utilized to express the disclosed polypeptides, including bacteria (e.g., *E. coli*), yeast, insect cells (e.g., Sf9 cells), or mammalian cells (e.g., 293 cells). In some examples, the polypeptide spontaneously assembles into a virus-like particle (VLP).

In some examples, the JCV VP1 polypeptide (or a fragment thereof), for example a capsid polypeptide comprising an amino acid sequence with at least 99% sequence identity to one or more of SEQ ID NOs: 1-15 and 27 (such as SEQ ID NO: 1, 2, 9-15, or 27), is administered to the subject as a part of a VLP, such as a JCV VLP. Immunogens are typically presented multimerically (e.g., about 72 pentamers or about 360 capsid polypeptides per VLP particle) to immune cells such as B cells and antigen presenting cells. This results in effectively inducing immune responses against the immunogen, in particular, antibody responses. In some examples, the VLP also includes a JCV VP2 and/or VP3 polypeptide. In specific embodiments, the antigen that is part of the disclosed VLPs includes one or more of the JCV VP1 polypeptides disclosed herein and has the ability to spontaneously assemble into VLPs. In one example, a VLP includes a JCV VP1 polypeptide (such as a VP1 polypeptide with at least 99% sequence identity to one of SEQ ID NOs: 1, 2, 9-15, or 27) and optionally a JCV VP2 polypeptide and/or JCV VP3 polypeptide.

In further examples, a fragment of a disclosed JCV VP1 polypeptide retains the ability to spontaneously assemble into VLPs. Fragments (such as immunogenic fragments) and variants can be of varying length. For example, a fragment may consist of six or more, 25 or more, 50 or more, 75 or more, 100 or more, or 200 or more amino acid residues of a JCV VP1 amino acid sequence. This includes, for example, any polypeptide six or more amino acid residues in length that is capable of spontaneously assembling into VLPs. Methods to assay for VLP formation and isolation of VLPs are well known in the art (see, for example, Pastrana et al., *PLoS Pathogens* 5(9):e1000578, 2009, herein incorporated by reference in its entirety).

V. Immunogenic Compositions and Modes of Administration

The JCV VP1 polypeptides (or fragments thereof) disclosed herein, or nucleic acids encoding the JCV VP1 polypeptides, can be used to elicit an immune response against JCV in a subject. In several examples, the subject is infected with at least one JCV genotype or is at risk of being infected with JCV. Thus, in several embodiments, the methods include administering to a subject an effective amount of an immunogenic composition including a JCV VP1 polypeptide or nucleic acid encoding a JCV VP1 polypeptide in order to elicit an immune response in the subject, such as, but not limited to, a neutralizing antibody immune response against JCV.

In the disclosed methods, compositions are administered to a subject in an amount sufficient to produce an immune response to a JCV. The disclosed JCV VP1 polypeptides, VLPs including the VP1 polypeptides, or polynucleotides encoding these polypeptides, are of use to inhibit (or even prevent) an infection with JCV in a subject, inhibit (or even prevent) progression to disease in a subject having a latent JCV infection, or to inhibit or treat PML in a subject infected with JCV. In several examples, administration of an effective amount of a composition including a JCV VP1 polypeptide (or fragment thereof) disclosed herein (or polynucleotides encoding these polypeptides) induces a sufficient immune response to decrease a symptom of a disease due to JCV infection (such as PML), to inhibit the development of one or more symptoms of PML or other JCV-associated disease (such as nephropathy), or to inhibit infection with JCV. In other examples, the compositions are of use in inhibiting or even preventing a future infection with JCV.

Thus, in some embodiments, an effective amount (such as an immunogenically effective amount or a therapeutically effective amount) of the composition is administered to a subject at risk of becoming infected with JCV or at risk of developing PML. In some examples the subject is an immunocompromised subject, a subject treated with or a candidate for treatment with immunosuppressant therapy, or a subject who does not have detectable levels of antibodies capable of neutralizing one or more (such as 2, 3, 4, 5, 6, 7, 8, or more) JCV genotypes, including JCV genotypes with mutant VP1 polypeptides. The composition inhibits the development of JCV infection, such as development of latent or active JCV infection, in the subject upon subsequent exposure to JCV, loss of immunological control over an existing JCV infection (for example reactivation of a latent infection), or development of PML or other JCV-associated disease.

In some examples, an effective amount is an amount sufficient to elicit an antibody response (such as a neutralizing antibody response) to one or more (such as 2, 3, 4, 5, 6, 7, or more) JCV genotypes, including JCV genotypes with a WT VP1 polypeptide or a VP1 polypeptide amino acid variant (such as a VP1 mutant associated with PML), or both. In other examples, an effective amount is an amount sufficient to inhibit an infection with JCV in a subject upon subsequent exposure of the subject to one or more JCV genotypes, or inhibit the emergence of an existing JCV infection from asymptomatic latency in a subject. In additional examples, an effective amount is an amount sufficient to inhibit development of one or more symptoms in a subject infected with JCV (for example, JCV-associated PML).

An immunogenic composition including one or more JCV VP1 polypeptides is thus provided. The immunogenic compositions may include, consist essentially or, or consist of one or more isolated VP1 polypeptides, such as one or more JCV genotype 1A, 1B, 2A, 2B, 2C, 3A, 3B, 4, 5, 6, 7A, 7B, 7C, 8A, or 8B VP1 polypeptides (such as a polypeptide with at least 99% sequence identity to SEQ ID NOs: 1, 2, 9-15, or 27). In some particular embodiments, the immunogenic composition includes one or more isolated JCV VP1 polypeptides (such as a JCV genotype 2 VP1 polypeptide and/or a JCV genotype 3 VP1 polypeptide) and a pharmaceutically acceptable carrier, such as a sterile solution suitable for administration to a subject. In other embodiments, the immunogenic composition includes one or more isolated JCV VP1 polypeptides (such as a JCV genotype 2 VP1 polypeptide and/or a JCV genotype 3 VP1 polypeptide) and an added adjuvant for increasing immunogenicity of the VP1 polypeptide(s). In additional embodiments, the immunogenic composition includes an isolated JCV genotype 2 VP1 polypeptide and or an isolated JCV genotype 3 VP1 polypeptide, one or more pharmaceutically acceptable carriers, and an added adjuvant (such as alum). In still further examples, the immunogenic composition also includes one or more added preservatives (including but not limited to thimerosal, phenol, benzethonium chloride, and 2-phenoxyethanol). In one example, an immunogenic composition includes an isolated JCV genotype 2A VP1 polypeptide and/or an isolated JCV genotype 3B VP1 polypeptide and alum (for example, about 0.2% aluminum hydroxide). One of skill in the art can select additional adjuvants for inclusion in an immunogenic composition, or for administration with the immunogenic composition, as discussed below.

In some examples, the disclosed compositions include a JCV VP1 polypeptide (or a fragment thereof) and a pharmaceutically acceptable carrier. In particular examples, the compositions include a VLP including a JCV VP1 polypeptide, such as a genotype 2 VP1 polypeptide (such as a genotype 2A VP1 polypeptide), a genotype 3 VP1 polypeptide (such as a genotype 3B VP1 polypeptide), a JC genotype 1 VP1 polypeptide (such as a genotype 1A VP1 polypeptide), or a combination thereof, and a pharmaceutically acceptable carrier. In some embodiments, the compositions also include one or more added adjuvants, preservatives, or detergents. Methods for preparing administrable compositions will be known or apparent to those skilled in the art and are described in more detail in such publications as *Remington: The Science and Practice of Pharmacy*, The University of the Sciences in Philadelphia, Editor, Lippincott, Williams, & Wilkins, Philadelphia, Pa., 21$^{st}$ Edition (2005). In particular examples, the immunogenic composition is sterile.

In some examples, the immunogenic composition includes a JCV VP1 polypeptide or fragment thereof described herein that may be covalently linked to at least one other immunogenic protein, wherein the conjugate elicits an immune response to the JCV VP1 polypeptide (for example, a neutralizing antibody) in a subject. The other immunogenic protein (sometimes referred to as a "carrier" protein) ideally has the properties of being immunogenic by itself, usable in a subject, and of a size that can be easily purified and conjugated to at least one other protein or peptide. Suitable carrier proteins are known to one of skill in the art. In particular examples, the other immunogenic protein (carrier protein) is bovine serum albumin (BSA), ovalbumin, tetanus toxoid, diphtheria toxoid, cholera toxin, *Clostridium difficile* toxin A, *C. difficile* toxin B, Shiga toxin, or *Pseudomonas aeruginosa* recombinant exoprotein A.

The JCV VP1 polypeptide or immunogenic composition can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular injection, subcutaneous injection, intraperitoneal injection, intravenous injection, oral administration, nasal administration, transdermal administration, or even anal administration. In some embodiments, administration is by oral administration, subcutaneous injection, or intramuscular injection.

To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release.

Aluminum salts (for example, aluminum hydroxide or aluminum phosphate) can also be used as adjuvants to produce an immune response. Additional exemplary adjuvants include pattern recognition receptor (PRR) ligands, for example, Toll-like receptor ligands (such as imiquimod, poly (I:C), monophosphoryl lipid A, bacterial flagellin, imidazoquinolines, or CpG oligodeoxynucleotides), NOD2 ligands (such as muramyl dipeptide or adamantylamide dipeptide), RIG-I-like receptor ligands, and C-type lectin receptor ligands. Water-in-oil emulsions (such as incomplete Freund's adjuvant) or oil-in-water emulsions (for example, squalene oil-in-water emulsions such as MF59®, AS03™, or AddaVax™ emulsions) are also adjuvants that can be used in the immunogenic compositions disclosed herein. One of skill in the art can identify additional suitable adjuvants (see, e.g., Vaxjo, available on the World Wide Web at violinet.org/vaxjo). In some examples, an adjuvant is included in an immunogenic composition, such as those disclosed herein. In other examples, an adjuvant is administered to a subject concurrently with (such as simultaneously or substantially simultaneously) the immunogenic composition. In other examples, an immunogenic composition and an adjuvant are administered to a subject sequentially.

Optionally, one or more cytokines, such as IL-2, IL-6, IL-7, IL-12, RANTES, GM-CSF, TNF-α, or IFN-γ, one or more growth factors, such as GM-CSF or G-CSF; one or more molecules such as OX-40L or 4-1 BBL, or combinations of these molecules, can be used as adjuvants (see, for example, Salgaller et al., 1998, *J. Surg. Oncol.* 68(2):122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host. In several examples, IL-2, IL-7, RANTES, GM-CSF, TNF-α, IFN-γ, G-CSF, LFA-3, CD72, B7-1, B7-2, B7-1 B7-2, OX-40L, 4-1 BBL, and/or ICAM-1 are administered, for example as part of an immunogenic composition, or in combination with an immunogenic composition.

In one embodiment, the JCV VP1 polypeptide or VLP is mixed with an aluminum adjuvant. In other embodiments, the JCV VP1 polypeptide or VLP is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977; and Hunter et al., *J. Immunol.* 127:1244-1250, 1981; for example, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immunol.* 133:3167-3175, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse effects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif, or a biological adjuvant (see above).

Controlled release parenteral formulations can be made as implants, oily injections, or as particulate systems. For an overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342; and 5,534,496).

In another embodiment, an immunogenic composition includes a nucleic acid encoding a JCV VP1 polypeptide or fragment thereof (such as a nucleic acid encoding a JCV genotype 1, 2, 3, 4, 5, 6, 7, or 8 VP1 polypeptide). In some examples, the immunogenic composition includes one or more isolated nucleic acids encoding a JCV genotype 2 VP1 polypeptide (such as a genotype 2A VP1 polypeptide) and/or a JCV genotype 3 VP1 polypeptide (such as a genotype 3B VP1 polypeptide) and a pharmaceutically acceptable carrier, an adjuvant, or a combination thereof. In some examples, the isolated nucleic acid(s) are included in a vector, such as a vector with a strong promoter and/or a polyadenylation signal. Exemplary vectors suitable for use in a nucleic acid immunogenic composition are described in Williams et al., *Biotechnol. Adv.* 27:353-370, 2009 and Williams, *Vaccines* 1:225-249, 2013. One of skill in the art can identify additional appropriate vectors for use in the immunogenic compositions and methods disclosed herein.

An effective amount of the JCV VP1 polynucleotide can be administered to a subject in order to generate an immune response. One approach to administration of nucleic acids is direct immunization with plasmid DNA, such as with a mammalian expression plasmid. For example, the nucleotide sequence encoding a JCV VP1 polypeptide (such as a nucleic acid with at least 90% identity to one of SEQ ID NOs: 16-26) can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™ (negatively charged cage-like structures of 30-40 nm in size formed spontaneously on mixing cholesterol and saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991).

Optionally, one or more cytokines, such as IL-2, IL-6, IL-7, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 4-1 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6(Suppl 1):561-6; Cao et al., 1998, *Stem Cells* 16(Suppl 1):251-60; Kuiper et al., 2000, *Adv. Exp. Med. Biol.* 465:381-90). These molecules can be administered systemically to the host. It should be noted that these molecules can be co-administered via insertion of a nucleic acid encoding the molecules into a vector, for example, a recombinant pox vector (see, for example, U.S. Pat. No. 6,045,802). In various embodiments, the nucleic acid encoding the biological adjuvant can be cloned into same vector as the JCV VP1 polypeptide coding sequence, or the nucleic acid can be cloned into one or more separate vectors for co-administration.

In one embodiment, a nucleic acid encoding a JCV VP1 polypeptide is introduced directly into cells. For example, the nucleic acid can be loaded onto gold microspheres by standard methods and introduced into the skin by a device such as the Helios™ Gene Gun (Bio-Rad, Hercules, Calif.). The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, for example, U.S. Pat. No. 5,589,466).

In one specific, non-limiting example, an immunogenic composition for injection (such as parenteral or intramuscular injection) would include about 0.1 μg to 100 mg of immunogenic JCV VP1 polypeptide (or fragment thereof) per patient per day. Dosages from 0.1 to about 100 mg per patient per day (for example, about 10 mg to 50 mg) can be used, particularly if the agent is administered to a secluded site and not into the circulatory or lymph system, such as into a body cavity or into a lumen of an organ. In other non-limiting examples, the pharmaceutical composition includes one or more VLPs including the disclosed JCV VP1 polypeptides, for example about 0.1 μg to 10 mg VLP (such as about 0.1 μg to 1 mg, 10 μg to 500 μg, about 20 μg to 100 μg, or about 20 μg to about 40 μg). In some embodiments, the disclosed immunogenic compositions can be formulated in unit dosage form, suitable for individual administration of precise dosages. In one specific, non-limiting example, a unit dosage contains from about 0.1 μg to 100 mg of immunogenic JCV VP1 polypeptide or from about 0.1 μg to 10 mg VLP containing JCV VP1 polypeptides. In some examples, a unit dosage contains about 0.1 μg, 0.5 μg, 1 μg, 2.5 μg, 5 μg, 10 μg, 25 μg, 50 μg, 75 μg, 100 μg, 200 μg, 500 μg, 1 mg, 10 mg, or 100 mg of JCV genotype 2 VP1 polypeptide (such as a genotype 2A VP1 polypeptide) and/or JCV genotype 3 VP1 polypeptide (such as a genotype 3B VP1 polypeptide). In other examples, a unit dosage contains about 0.1 μg, 0.5 μg, 1 μg, 10 μg, 25 μg, 50 μg, 100 μg, 200 μg, 500 μg, 750 μg, 1 mg, 2.5 mg, 5 mg, or 10 mg of a VLP including at least one JCV VP1 polypeptide. In some embodiments, the immunogenic composition is provided as a unit dose in a syringe (for example, for intramuscular or subcutaneous administration).

In one embodiment, the dosage is administered once as a bolus, but in another embodiment can be applied periodically until a therapeutic result is achieved. In one embodiment, the dose is sufficient to treat or ameliorate symptoms or signs of JCV without producing unacceptable toxicity to the subject. In another embodiment, the dose is sufficient to inhibit infection with JCV upon subsequent exposure to JCV. In a further embodiment, the dose is sufficient to inhibit a symptom of PML in a subject with a latent JCV infection. Systemic or local administration can be utilized.

In some examples, the effectiveness of the therapeutic or preventive intervention is monitored by tittering the JCV neutralizing potential of the subject's serum antibody responses over time (for example, using the methods described in Example 1 herein). Subjects who are found to have been poorly responsive to initial immunization with JCV VP1 polypeptides are given one or more booster doses of the therapeutic intervention.

Repeated immunizations may be used to produce or enhance an immune response in a subject. In some examples, at least one booster dose is administered to a subject, for example to produce or increase titer of PML-variant JCV neutralizing antibodies. When administered in multiple doses, the booster doses can be administered at various time intervals, such as weeks to months. In one example, a subject is administered a prime dose of a JCV VP1 immunogenic composition followed by at least one boost dose of one or more of the JCV VP1 immunogenic compositions disclosed herein. In some examples, a boost dose is administered about 7, 14, 21, 28, or more days after administration of the prime dose. In other examples, a boost dose is administered about 6 weeks, 8 weeks, 12 weeks, 16 weeks, 20 weeks, 24 weeks, or more after administration of the prime dose. Additional boosters can be administered at subsequent time points, if determined to be necessary or beneficial. Immunization protocols (such as amount of immunogen, number of doses and timing of administration) can be determined experimentally, for example by using animal models (such as mice or non-human primates, for example, as described in Section VII and Examples 3 and 4 herein), followed by clinical testing in humans.

VI. Methods of Identifying Subjects at Risk for PML

Disclosed herein are methods for identifying subjects at risk for developing PML. This information can be useful for making decisions regarding whether or not to treat a subject with immunosuppressants (for example, immunosuppressants known to be associated with PML risk) or whether an immunocompromised subject (including one being treated with immunosuppressants) is at risk for or should be monitored for symptoms of PML. In addition, a subject who is at risk for PML is a candidate for immunization against JCV, for example utilizing the methods and compositions disclosed herein.

In some embodiments, methods of identifying a subject at risk for developing PML include obtaining a biological sample from a subject and detecting presence or absence or amount of detectable JCV neutralizing antibodies in the sample from the subject. If there is a low amount or an absence of detectable JCV neutralizing antibodies in the sample (for example, absence of detectable levels of neutralizing activity against one or more JCV genotypes or against one or more PML-associated mutant JCV genotypes), the subject is identified as at risk of developing PML. In a particular example, a subject is considered to be at risk of PML if their serum has a low (for example, <100 ($<\log_{10}$ $EC_{50}$)) or undetectable neutralizing titer against one or more JCV genotypes (for example, a JCV genotype carrying a PML-associated mutation, such as L55F, S269F, N265S, S267F, Q271H, or other PML-associated mutations shown in Table 4). In additional examples, a subject is identified as being at risk of developing PML if there is low or undetectable neutralization of the PML-associated mutant even if presence of detectable WT JCV neutralizing antibodies are present in the sample from the subject. A biological sample from a subject of use in the disclosed methods can include any fluid or tissue sample which could contain an antibody, such as cerebrospinal fluid, blood, bile plasma, serum, saliva, urine, sputum, mucus and the like.

Methods for detecting antibodies in a sample are known to one of skill in the art. Such methods include but are not limited to ELISA, immunofluorescence assay, radioimmunoassay, and micro-agglutination test. In some examples, the methods include detecting the presence of neutralizing antibodies (such as JCV neutralizing antibodies) in a sample from a subject. Assays for detecting neutralizing antibodies include but are not limited to the JCV neutralization assay described herein (Example 1), plaque reduction neutralization test, cell killing, quantitation of viral DNA replication or viral RNA transcription, and reporter assays.

In a particular example, neutralizing antibodies are detected using a JCV reporter vector assay. JCV reporter vectors (also known as pseudovirions) are produced by packaging a reporter plasmid (or plasmids) in cells (such as 293TT cells or the ART, SFT, or SNBT cells described in Example 1) expressing JCV capsid polypeptides (for example, VP1, VP2, and/or VP3). The reporter vector particles encapsidate a reporter plasmid carrying a eukaryotic reporter gene expression cassette. Assembled pseudovirions are isolated and treated with serial dilutions of serum from a subject (such as a series of four-fold dilutions from 1:50 to $1:3.3\times10^6$ or a series of 10-fold dilutions from 1:100 to $1\times10^7$). The serum/reporter vector mixture is then applied to fresh cells (such as ART, SFT, SNBT, or 293TT cells) for a period of time (such as five days). The cell culture is then assayed for production of a reporter protein encoded by the reporter plasmid packaged within the reporter vector. A decrease in reporter gene activity (for example, as compared to a control, such as a no serum control) indicates the presence of neutralizing antibodies in the sample. In one example, the reporter plasmid carries an SV40 origin of replication, which can mediate replicative amplification of the transduced plasmid in the transduced target cell. Reporter genes of use in neutralizing antibody assays include luciferase, green fluorescent protein, β-galactosidase, alkaline phosphatase, and others.

In some examples, the methods further include administering to a subject identified as being at risk for developing PML an immunogenic composition including one or more isolated JCV VP1 polypeptides (such as an isolated JCV genotype 2A VP1 polypeptide, an isolated JCV genotype 3B VP1 polypeptide, and/or an isolated JCV genotype 1A VP1 polypeptide), VLPs including one or more JCV VP1 polypeptides, or an isolated nucleic acid encoding the VP1 polypeptide(s), for example to elicit an immune response against JCV (for example, as disclosed herein). The immune response elicited by the immunogenic composition (such as a neutralizing antibody response) can inhibit or prevent infection of the subject with JCV or development of PML if the subject is infected with JCV. Immunogenic compositions and methods of their administration of use in a subject identified as being at risk for developing PML are described above.

VII. Methods of Evaluating Candidate Vaccine Efficacy

The JCV neutralization assay disclosed herein may be used in methods to assess the efficacy of candidate JCV vaccines, including, but not limited to, the JCV immunogenic compositions disclosed herein. Currently, it is difficult to test the efficacy of candidate JCV immunogenic compositions or vaccines because high-throughput systems for quantitative analysis of JCV-neutralizing antibodies are not available. Furthermore, it has previously been believed that JCV with PML-associated mutant VP1 polypeptides are not infectious (e.g. Maginnis et al., *MBio* 4:e00247, 2013). However, it is demonstrated herein that various PML mutants, including S269F, can infect several previously untested cell lines. This provides a method for testing the infectivity of various PML-associated mutants, including (but not limited to) S269F. The ability to measure the infectivity of PML mutants in turn provides methods for identifying antibodies or other agents capable of neutralizing the infectivity of PML-associated mutant JCVs. The neutralization assay described herein allows rapid and efficient screening for JCV-neutralizing antibody responses against both WT and PML-associated mutant JCVs. Thus, in one example, the samples (such as serum samples) from subjects who have been administered a JCV immunogenic composition could be tested to quantitate the level of JCV-neutralizing serum antibodies.

The efficacy of candidate JCV vaccines or immunogenic compositions may be tested by inoculating subjects (for example, hamsters, mice, rabbits, non-human primates, or human subjects) with one or more doses of a candidate JCV immunogenic composition. After a period of time sufficient to allow development of a neutralizing antibody response (such as at least about 1 week, 2 weeks, 3 weeks, 4 weeks, 6 weeks, 2 months, 3 months, 6 months, or more), samples are collected from the subject (for example, serum samples) and tested with a neutralizing antibody assay, such as that described herein. Identification of neutralizing antibodies in the sample by the assay indicates the efficacy of the JCV immunogenic composition. In some examples, presence of antibodies capable of neutralizing JCV (for example, one or more WT or PML-associated mutant JCV genotypes) with a neutralizing titer of at least 100, such as at least 100, 1000, 10,000, or more ($\log_{10}$ $EC_{50}$ at least 2, 3, 4, or more) indicates that the candidate JCV immunogenic composition is effective.

In one particular embodiment, a set of subjects (such as mice) is inoculated with a candidate JCV vaccine (for example, an immunogenic composition including one or more JCV VP1 polypeptides). Administration of the candidate vaccine may be carried out by any suitable means, including parenteral injection (such as intraperitoneal, subcutaneous, or intramuscular injection). In a particular example, the subjects are inoculated intraperitoneally with an immunogenic composition including a JCV VP1 polypeptide or fragment thereof in a vehicle such as phosphate buffered saline. In some examples, the immunogenic composition also includes one or more adjuvants, such as alum, Freund's complete adjuvant or Freund's incomplete adjuvant. Multiple inoculations (such as boosters) may be carried out, separated by a suitable period of time, such as at least one week, two weeks, three weeks, four weeks, eight weeks, twelve weeks, or more. Samples (such as serum samples) from the subjects are tested for the presence of JCV neutralizing antibodies using the JCV reporter vector assay described in Section V and Example 1 herein.

A decrease in the expression of the reporter gene compared to a control (for example, a decrease of at least 10%, 20%, 30%, 40%, 50%, 60%, 70%, 80%, 90%, 95%, or 99% compared with a control) indicates the presence of neutralizing antibodies in the sample from the subject and the effectiveness of the candidate vaccine. In some examples, the control includes cells contacted with JCV pseudovirus/reporter plasmid alone (for example, not contacted with a serum sample ("no serum" control)) or cells contacted with JCV pseudovirus/reporter plasmid and control serum (such as serum from one or more subjects not inoculated with the candidate JCV vaccine), or a reference value (such as a no serum reference value). In other examples, the methods include determining a neutralizing antibody titer in the subject (for example by using serial dilutions of serum in the assay) and an increase in neutralizing antibody titer compared to a control (for example, an increase of 1.2-fold, 1.5-fold, 2-fold, 3-fold, 5-fold, 10-fold, 25-fold, 50-fold, 100-fold, or more) indicates the effectiveness of the candidate vaccine. In further examples, an increase in neutralizing antibody titer compared to a reference or cutoff value indicates the effectiveness of the candidate vaccine. In some examples, presence of antibodies capable of neutralizing JCV (for example, one or more WT or PML-associated mutant JCV genotypes) with a neutralizing titer of at least 100 (such as at least 100, 1000, 10,000, or more) indicates that the candidate JCV immunogenic composition is effective. In one non-limiting example, a candidate JCV immunogenic composition is determined to be effective if it elicits serum neutralizing antibodies against at least two JCV genotypes (including WT and PML-associated genotypes), such as at least 2, 3, 4, 5, 6, 7, 8, 9, 10, or more genotypes with neutralizing titers of at least 500.

In another embodiment, neutralization assays, such as (but not limited to) the ones described herein, are used to characterize antibody preparations, including either bulk human immunoglobulins, human monoclonal antibodies, or humanized monoclonal antibodies, that might be capable of neutralizing JCV. Such antibody preparations could be used for prevention or treatment of JCV disease, such as PML. In some examples, a neutralizing titer of at least 100 (such as at least 100, 1000, 10,000, or more) indicates that the antibody preparation could be useful to treat or prevent JCV infection or PML. In some examples, the antibody preparation has neutralizing titers of at least 500 against one or more WT or PML-associated mutant JCV genotypes (including, but not limited to JCV L55F and/or S269F PML-associated JCV mutants).

The present disclosure is illustrated by the following non-limiting Examples.

Example 1

Materials and Methods

Pseudovirus Production:

JCV isolates are traditionally classified into seven genotypes (Agostini et al., *J. Gen. Virol.* 82:1221-1231, 2001). A codon-modified (Pastrana et al., *Virology* 321:205-216, 2004) expression plasmid encoding the VP1 protein of a JCV genotype 2A primary isolate derived from the urine of a healthy subject (SEQ ID NO: 1) was initially generated for production of a model wt JCV pseudovirus (Table 4). An expression plasmid representing the VP1 of a phylogenetically divergent urine-derived genotype 3B primary isolate was also constructed. Characteristic PML mutations were introduced into the 2A or 3B background using PCR-based mutagenesis. In some instances, mutations representing PML patient isolate VP1 sequences were introduced into the background of the lab-adapted JCV isolate Mad1 (genotype 1A) (Maginnis et al., *mBio* 4:e00247-13, 2013). All pseudoviruses employed the VP2 and VP3 minor capsid proteins of JCV strain 313B (accession AAK28470), a genotype 3B isolate. The expression plasmids were used to produce reporter pseudovirions in 293TT cells (Buck et al., *J. Virol.* 78:751-757, 2004) according to previously reported methods (Pastrana et al., *PLoS Pathogens* 5:e1000578, 2009; Pastrana et al., *J. Virol.* 87:10105-10113, 2013).

Pseudovirions were produced with a mixture of two separate reporter plasmids, phGluc (*Gaussia* luciferase (Gluc) under control of EF1α promoter) and pCGluc (Gluc under control of CMV immediate early promoter). Neuraminidase V and RNase were used during the pseudovirion harvest. After clarification of the cell lysate, the pelleted cell debris was washed with DPBS containing 0.8 M NaCl with 1% Triton X-100, with the goal of extracting any entrapped pseudovirions. VLPs were produced using similar methods, except the cells were transfected only with the relevant VP1 expression plasmid and the cell lysate was supplemented with Benzonase endonuclease (Sigma-Aldrich, St. Louis, Mo.). After OptiPrep™ gradient (Sigma-Aldrich) purification of pseudovirions or VLPs, VP1 content was assessed by comparison to BSA standards in SDS-PAGE gels stained with SYPRO® Ruby dye (Invitrogen/Life Technologies, Grand Island, N.Y.) or by western blot comparisons using a blend of sera from JCV VLP-immunized mice (see below).

Sera:

Anonymized human serum samples (24) used for initial validation of the neutralization assay were provided under the auspices of the second meeting of the Standardization of JCV Serology Workshop. Serum samples were heat-inactivated at 56° C. for 30 minutes, followed by brief centrifugation to sediment any aggregated material.

A previously described panel of 96 anonymized sera from healthy human subjects were purchased from Equitech-Bio (Kerrville, Tex.) and Innovative Research (Novi, Mich.) (see also, Pastrana et al., *PLoS Pathogens* 5:e1000578, 2009). Serum IgG antibodies were purified out of the serum samples using Melon™ Gel resin (Pierce/Thermo Scientific, Rockford, Ill.) according to the manufacturer's instructions. Sera were first buffer-exchanged into Melon™ Gel purification buffer using a Zeba™ 96-well spin desalting plate (40K MWCO; Pierce/Thermo Scientific, Rockford, Ill.). Buffer-exchanged samples were then loaded onto a 96-well Melon™ Gel spin plate. Finally, the Melon™ Gel-purified antibody samples were buffer exchanged into PBS using a Zeba™ 96-well spin desalting plate.

TABLE 4

Characteristics of JCV pseudovirus stocks

| Genotype | Differences relative to 2A | VP1 stock (ng/μl) | VP1 dose (ng/well) | ART RLU × $10^{-5}$ | SFT RLU × $10^{-5}$ |
|---|---|---|---|---|---|
| 2A (wt) | None, accession AAK97910 (SEQ ID NO: 1) | 0.9 | 0.2 | 4.1 ± 1.3 | 2.8 ± 0.7 |
| 3B (wt) | G134A, K164T, V321I, E332Q (SEQ ID NO: 2) | 3.9 | 0.4 | 5.1 ± 0.9 | 3.8 ± 0.4 |
| 3B-55F | 3B + L55F (SEQ ID NO: 3) | 2.4 | 0.2 | 4.7 ± 0.6 | 8.1 ± 2.7 |
| 3B-265S | 3B + L55F, N265S (SEQ ID NO: 4) | 2.4 | 0.2 | 2.5 ± 0.5 | 5.1 ± 1.2 |
| 2A-267F | S267F, Q271H (SEQ ID NO: 5) | 6.0 | 1 | 3.2 ± 0.4 | 6.0 ± 1.0 |
| 3B-267F | 3B + S267F, Q271H (SEQ ID NO: 6) | 3.0 | 0.6 | 0.6 ± 0.4 | 0.7 ± 0.1 |
| 2A-269F | S269F (SEQ ID NO: 7) | 1.9 | 0.2 | 3.1 ± 0.7 | 5.9 ± 0.9 |
| 3B-271K† | 3B + L55F, Q271K (SEQ ID NO: 8) | 1.8 | nd | nd | nd |
| GCN1 | Y346* (SEQ ID NO: 9) | 0.5 | 0.05 | 1.0 ± 0.8 | 0.1 ± 0.2 |
| 1A (Mad1) | K75R, T117S, V158L, R345K (SEQ ID NO: 27) | nd | (1:500 diln) | nd | nd |
| 5029w | N74T, T128A, R345K | 2.0 | 0.2 | 3.5 ± 1.6 | nd |
| 5029m | 5029w + S269F | 18 | 2.2 | 2.6 ± 0.9 | nd |
| 5031w | 3B | 3.9 | 0.4 | 5.1 ± 0.9 | 3.8 ± 0.4 |
| 5031ma | 3B-55F | nd | (1:150 diln) | 1.03 ± 0.2 | nd |
| 5031mb | 3B + Q271H | 2.4 | 0.2 | 4.7 ± 0.6 | 8.1 ± 2.7 |
| 5031mc | 3B + L55F, Q271H | nd | (1:150 diln) | | nd |
| 5040w† | 1A + T128S | nd | nd | nd | nd |
| 5040m | 5040w + H122R | 2.0 | 0.2 | 4.0 ± 0.7 | nd |
| 5053w | T128A, R345K | nd | (1:800 diln) | 2.3 ± 0.8 | nd |
| 5053m | 5053w + L55F | nd | (1:400 diln) | 1.7 ± 0.7 | nd |
| 5058w† | 2A? + T117S, V158L | nd | nd | nd | nd |
| 5058m | 5058w + S269F | nd | nd | nd | nd |
| 5147w | 5053w [F171S?, T232N?, L252del?] | nd | (1:800 diln) | 2.3 ± 0.8 | nd |
| 5147m | 5053w + S269F | 18 | 2.2 | 2.1 ± 0.5 | nd |
| 5228w | 5053w | nd | (1:800 diln) | 2.3 ± 0.8 | nd |
| 5228m | 5053w + S269F | 18 | 2.2 | 2.1 ± 0.5 | nd |

"m" indicates PML-associated mutation, "w" indicates WT, "b" and "c" represent additional PML-associated mutations observed in patient 5031's CSF
†Pseudovirus was either not generated or had unusably low titer.
?Incomplete or uncertain sequencing. Variations with incomplete sequencing support were not incorporated into the pseudovirus.
nd, not determined
Quadruplicate testing of the standard dose on ART or SFT cells yielded the number of Plasma (EDTA) samples from PML patients (Table 5) were collected under the approval of the ethical review board of the San Raffaele Scientific Institute, Milan, Italy. All time points for all PML patients tested seropositive in a JCV VP1 ELISA. PML patient plasma samples and mouse serum samples were heat inactivated at 56° C. for 30 minutes and tested without Melon™ Gel purification.

TABLE 5

PML patient characteristics

| ID# | Gender | Age at PML | PML diagnosis | Underlying disease | VP1 mutation | Date of death | CD4 + cells/μL[a] |
|---|---|---|---|---|---|---|---|
| 5029 | M | 36 | Jun. 1, 1996 | HIV | S269F | Oct. 30, 1996 | 14 |
| 5031 | M | 34 | Jan. 1, 1997 | HIV | L55F Q271H | Apr. 24, 1997 | 20 |
| 5040 | M | 34 | Jan. 7, 1997 | HIV | H122R, N265T, S269F | Feb. 21, 2006 | 122 |
| 5053 | M | 35 | Apr. 23, 1997 | HIV | L55F | | 53 |
| 5058 | F | 32 | Jul. 1, 1997 | HIV | S269F | | 162 |
| 5147 | M | 33 | Jan. 15, 2005 | HIV | S269F | May 15, 2005 | 7 |
| 5228 | F | 74 | May 24, 2012 | idiopathic CD4 lymphopenia | S269F | | 298 |

[a]CD4 count at the time of PML diagnosis

Neutralization Assays:

To test the idea that tropism of PML-mutant JCV strains is restricted to a range of as yet unidentified cell types the transducibility of a diverse range of cell lines with wt JCV-2A pseudovirus or with a pseudovirus carrying a representative PML-associated mutation, S267F (Table 4) was tested. Cell lines previously shown to be readily transducible with a BK polyomavirus (BKV) pseudovirus or a pseudovirus based on Merkel cell polyomavirus (MCV) were favored, based on the presumption that these lines lack innate antiviral defenses against polyomavirus-mediated transduction Schowalter et al., *PLoS One* 7:e42181, 2012). The classic cell lines Vero and SVG-A (Henriksen et al., *J. Virol.* 88:7556-7568, 2014) did not support efficient transduction with the 2A-267F mutant pseudovirus (data not shown). 293TT cells were only marginally permissive for PML-mutant JCV pseudoviruses (data not shown).

Three cell lines, NCI/ADR-RES (an ovarian tumor line similar to OVCAR-8 (Roschke et al., *Cancer Res.* 63:8634-8647, 2003; Garraway et al., *Nature* 436:117-122, 2005)), SF-539 (a gliosarcoma line (Rutka et al., *Cancer Res* 46:5893-5902, 1986)), and SNB-75 (a glioblastoma line (Gross et al., *Cancer Res.* 48:291-296, 1988)), were each found to be similarly transducible with both the 2A and 2A-267F pseudoviruses. This confirms that PML-mutant JCV strains are potentially infectious on a restricted range of cell types. Each of the three permissive cell lines were stably transfected with pTIH, which encodes the cDNA of SV40 Large T antigen (LT), with the goal of amplifying successfully transduced reporter pseudogenomes. Use of the SNB-75-LT (SNBT) cell line was discontinued due to its slow growth rate.

Additional PML-mutant pseudoviruses were applied to NCI/ADR-RES-LT (ART) and SF-539-LT (SFT) cell lines. Gluc assays (New England Biolabs, Ipswich, Mass.) were used to detect reporter gene activity in culture supernatants sampled at day 5 or 6 post-inoculation. Each of the pseudoviruses gave readily measurable transduction of both cell lines, except the 3B-271K mutant, which gave very low Gluc luminometry values (Table 4).

Neutralization assays were conducted using ART cells, essentially as previously described for BKV (Pastrana et al., *J. Virol.* 87:10105-10113, 2013). The 50% neutralizing titers were calculated using GraphPad Prism software (GraphPad, La Jolla, Calif.) to fit a sigmoidal dose-response curve, with top and bottom constrained based on "no antibody" and "no virus" controls, respectively. In initial setup experiments examining a set of six representative human sera, the 2A and 2A-267F pseudoviruses were applied to ART cells at various VP1 doses spanning a five-fold range. $EC_{50}$ titers for each of the six human sera were similar with different pseudovirion doses, suggesting that the neutralization assay complies with the assumptions of the law of mass action (Pierson et al., *Virology* 346:53-65, 2006).

Heat Map:

A heat map depicting serological results was generated using a hierarchical clustering heat map construction tool from the HIV sequence database website (hiv.lanl.gov/content/sequence/HEATMAP/heatmap.html).

Mouse VLP Immunization:

Mouse immunization experiments were performed at NCI facilities under the approval of the Animal Care and Use Committee and according to the guidelines of the Association for Assessment and Accreditation of Laboratory Animal Care International. Procedures were carried out in accordance with the eighth edition of the National Research Council of the National Academies' Guide for the Care and Use of Laboratory Animals. Female BALB/cAnNCr mice were subjected to intramuscular immunization with 720 ng of JCV VLPs (VP1 only) mixed with 0.2% of aluminum hydroxide (alum, InvivoGen, San Diego, Calif.). Each JCV VLP type was administered to a group of five replicate mice. One month after the single priming dose of VLPs, plasma samples were collected by sub-mandibular bleed into Microtainer® lithium-heparin tubes (Becton Dickinson, Franklin Lakes, N.J.). The mice were then boosted with the same JCV VLP type intramuscularly in alum. Serum samples were collected one month after the booster dose.

Vaccination Case Study:

Patient 5228 presented with an altered gait, and a CT scan had revealed a hypodense right temporal-parietal-occipital lesion that was initially interpreted to be of ischemic origin. Progression of symptoms and of brain lesions by MRI was monitored during subsequent weeks. About one month later, JCV DNA was detected in CSF (16,650 copies/ml) and the patient was diagnosed with PML and admitted at the Department of Infectious Diseases of San Raffaele Hospital, Milan, Italy. The patient's clinical condition deteriorated rapidly and she became comatose. A 1250 mg induction dose of mefloquine was given on two consecutive days about 5 weeks after presentation, then 500 mg twice a week from for the next two weeks. Mirtazapine (15 mg) was given daily from for the first 9 days after administration of mefloquine. Recombinant IL-7 was given subcutaneously at 10 µg/kg weekly for three weeks starting one week after first dose of mirtazapine (first cycle) and again for three weeks four months later. Subcutaneous injection of 1 mg of JCV-1A VLP was performed 26 days after first dose of mirtazapine, and boosted eight days and six weeks later. Imiquimod cream (5%, Aldara, MEDA Pharm, Germany) was applied as a vaccine adjuvant topically at the injection site. The treatments appeared to be well tolerated.

Example 2

Neutralization Serology

Pseudovirus-based infectivity assays can be used to quantitate the effects of virus-neutralizing antibodies present in human serum (Pastrana et al., *Virol.* 321:205-216, 2004; Pastrana et al., *Virol.* 405:20-25, 2010). In initial pilot experiments, a set of 24 serum samples from healthy individuals were each subjected to serial dilution, mixed with WT JCV genotype 2 or genotype 3 pseudovirus, and the mixtures were applied to SFT or ART cells. Expression of the GLuc reporter gene was measured 5-6 days after pseudovirion/antibody inoculation and the results were used to calculate a 50% inhibitory dilution ($EC_{50}$) for each dilution series. The calculated neutralizing $EC_{50}$ titers for each serum sample were similar using either ART or SFT target cells (FIGS. 2A and B). Serum samples from mice primed with JCV VLPs likewise showed similar neutralizing activity on both ART and SFT cells. Subsequent experiments with human serum samples used ART cells, which are somewhat faster growing than SFT and also appeared to give somewhat more reproducible $EC_{50}$ values in initial pilot experiments.

Serum antibody samples from 96 healthy human subjects were screened for neutralization of various JCV pseudoviruses. Consistent with prior ELISA-based studies, 60/96 (63%) of the subjects tested seropositive for neutralization of the WT JCV genotype 2 pseudovirus (Table 4, FIG. 3). Each genotype 2-neutralizing sample was further tested against various JCV pseudoviruses. Although a majority of samples that neutralized JCV genotype 2 also neutralized all other pseudoviruses with similar titers, a minority of sera failed to neutralize one or more of the PML VP1 mutant pseudoviruses. In particular, 11/60 2A seropositive sera failed to neutralize the 2A-269F pseudovirus, which represents the most common mutation observed in the CSF of PML patients (Gorelik et al., *J. Infect. Dis.* 204:103-114, 2011; Reid et al., *J. Infect. Dis.* 204:237-244, 2011). Surprisingly, the GCN1 mutant, which carries a VP1 C-terminal truncation (Dang et al., *J. Gen. Virol.* 87:2533-2537, 2006), appeared to be more susceptible to neutralization than all other tested pseudoviruses.

The results suggest that some individuals who are seropositive for neutralization of WT JCV nevertheless lack serum antibodies capable of neutralizing a subset of PML-mutant pseudoviruses. This is consistent with the idea that VP1 mutations found in the CSF of PML patients could, in addition to altering infectious tropism, give the virus a selective advantage by conferring escape from the apparently limited spectrum of JCV-neutralizing serum antibodies found in some JCV-seropositive individuals.

Example 3

JCV VLPs Elicit Cross-Neutralizing Antibodies in Mice

Figure 4:
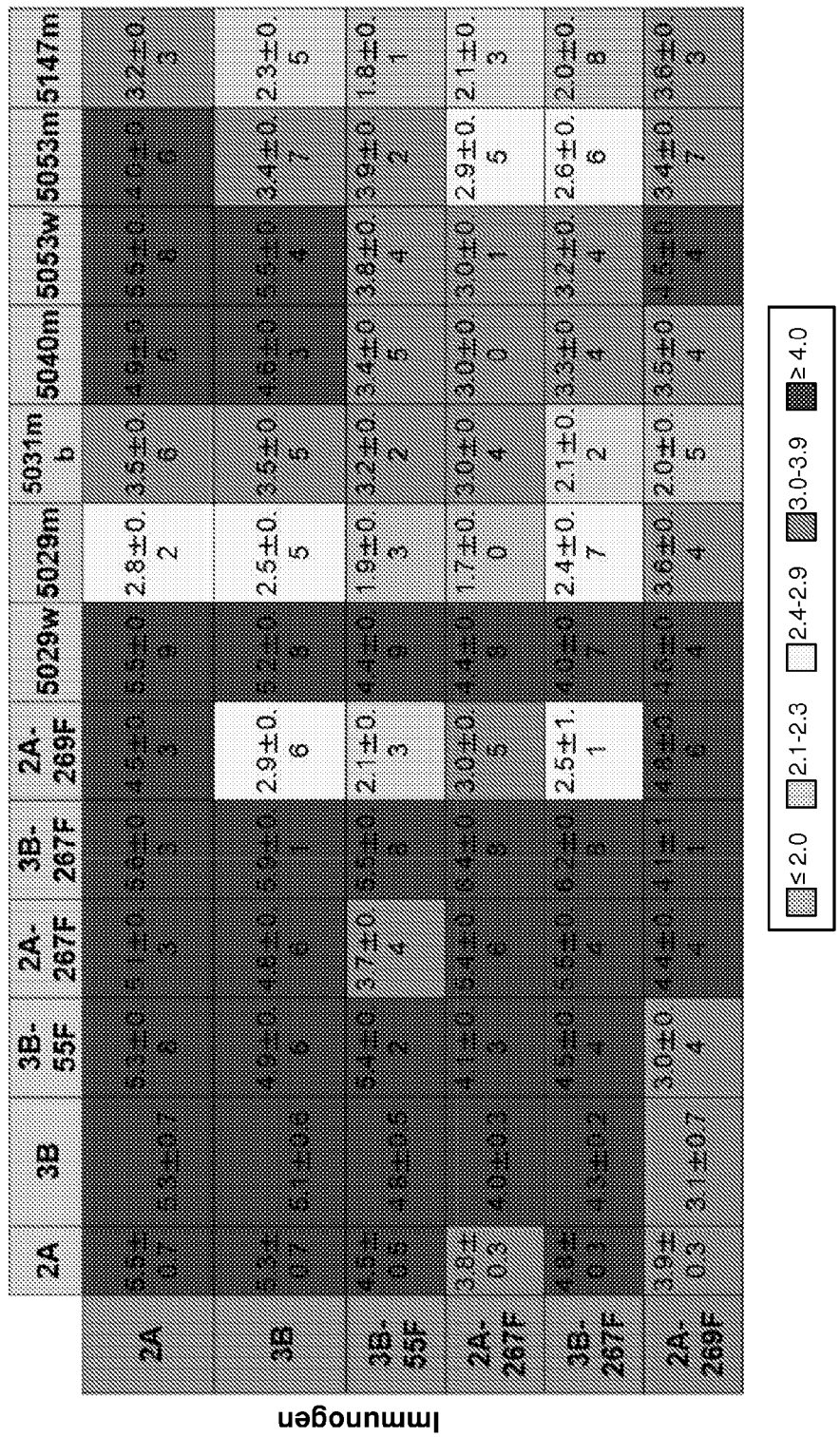
FIG. 4 is a diagram showing JCV-neutralization serology results for mice one month after administration of a single dose of 720 ng of JCV VLPs in alum. Rows (marked "Immunogen") represent the JCV genotype used to make the VLP immunogen. Columns indicate the JCV genotype used for the neutralization assay. Numbers are $\log_{10} EC_{50}$ values. Each cell represents the average of four or five individual mice. Error is standard deviation.

To test the idea that a JCV VLP might elicit broadly cross-neutralizing antibody responses, groups of mice were given a single intramuscular dose of 720 ng of a monovalent VLP preparation in alum. Pre-immune sera did not detectably neutralize any of the pseudoviruses. A single priming dose of VLP immunogen elicited high tier serum antibody responses capable of robustly neutralizing the cognate pseudovirus (Table 6, FIG. 4). Interestingly, each set of primed mice failed to robustly cross-neutralize at least one non-cognate pseudovirus type (FIG. 4). This result appears to recapitulate the neutralization blind spot effects observed in human subjects.

Mice were administered a booster dose of the same monovalent VLP preparation. Sera from all boosted animals cross-neutralized all tested JCV variants (FIGS. 5A-5D). Thus, it appears that blind spots can be closed through booster vaccination with a monovalent JCV VLP vaccine. Without being bound by theory, it is believed that human subjects who have JCV-neutralizing blind spots might experience closure of blind spots (e.g., develop broader humoral responses capable of cross-neutralizing all JCV genotypes) after vaccination with a JCV vaccine.

Overall, the wt 2A VLPs elicited the most uniformly robust cross-neutralizing responses, suggesting that it is not necessary (and possibly undesirable) to use PML-mutant VLP immunogens to elicit antibodies capable of neutralizing PML-mutant pseudoviruses. For example, the WT JCV 2A VLP immunogen is capable of eliciting broadly cross-reactive antibody responses that are capable of neutralizing the full spectrum of JCV genotypes. The data show that the WT JCV 2A VLP immunogen was superior (in terms of eliciting a broadly cross-neutralizing antibody response) to several of the PML-associated mutant JCV VLP immunogens. Thus, WT JCV immunogens appear to be preferable over PML-mutant immunogens.

TABLE 6

| Neutralization serology in SFT cells | | | | | |
|---|---|---|---|---|---|
| Neutralization Serology | JCV-2 | JCV-3 | 55F | 267F | 267F3B |
| VLP Immunogen | | | | | |
| JCV-2 | 5.3 ± 0.4 | 4.7 ± 0.6 | 5.3 ± 0.7 | 4.7 ± 0.5 | 5.7 ± 0.6 |
| JCV-3 | 4.6 ± 0.4 | 4.9 ± 0.9 | 4.5 ± 0.6 | 4.1 ± 0.3 | 5.6 ± 0.7 |
| 55F | 4 ± 0.7 | 4.6 ± 0.4 | 4.9 ± 0.9 | 3.4 ± 0.7 | 4.1 ± 0.6 |
| 267F | 4.4 ± 0.1 | 4 ± 0.7 | 6.5 ± 1.6 | 4.8 ± 0.2 | 4.1 ± 0.3 |
| 267F3B | 4.2 ± 0.5 | 4.2 ± 0.2 | 4.6 ± 0.2 | 5.1 ± 0.1 | 5.8 ± 0.1 |

Groups of five mice were immunized with VLPs based on the JCV genotype indicated in the row labels. One month post-priming, plasma samples from the immunized mice were tested in neutralization assays against JCV pseudoviruses indicated in the column labels. Each cell shows the average of the $\log_{10} EC_{50}$ for the group of five mice, with standard deviation.

Example 4

JCV VP1 Polypeptide Elicits Cross-Neutralizing Antibodies in Rabbits

Expression constructs encoding either WT JCV genotype 2 VP1 polypeptide or the PML-associated 267F VP1 polypeptide mutant fused to maltose binding protein (MBP) were generated using plasmid pMXB10 (New England Biolabs, Ipswich, Mass.). MBP-VP1 fusion proteins were expressed in T7 Express *E. coli* and purified over amylose resin according to the manufacturer's instructions (New England Biolabs, Ipswich, Mass.). The purified fusion proteins, which based on prior studies presumably adopted the form of JCV VP1 pentamers (also known as capsomers), were treated with tobacco etch virus (TEV) protease expressed from plasmid pRK792 (Kapust et al., *Protein Eng.* 14:993-1000, 2001). TEV protease cleaves apart the MBP fusion partner from VP1, potentially allowing at least partial assembly of VP1 into VLPs. Neither the MBP fusion partner nor the TEV protease was removed from the immnogen stock.

Rabbit immunizations were performed by Lampire Biological Laboratories (Pipersville, Pa.). Rabbits were administered three 0.5 mg doses of antigen on a three week interval. The initial priming dose was in complete Freund's adjuvant and the booster doses were in incomplete Freund's adjuvant. Hyperimmune sera were collected two months after the initial immunization.

A rabbit hyper-immunized with the JCV genotype 2 VP1 immunogen showed a serum neutralizing titer of 28,000 against the cognate JCV 2, and a robust cross-neutralizing titer of 18,000 against the JCV 267F mutant VP1 virus. Surprisingly, the rabbit hyper-immunized with the JCV-267F VP1 immunogen displayed very poor neutralizing titer against both viruses (140 against JCV-2 and 800 against JCV-267F). These data indicate that, in this setting, elicitation of high titer antibody responses capable of cross-neutralizing different JCV genotypes is more effectively achieved through immunization with a WT JCV VP1 immunogen than immunization using a PML-associated mutant JCV VP1 immunogen.

Example 5

Pseudovirus Neutralization by PML Patient Samples

This example describes the ability of serum samples from PML patients to neutralize cognate and non-cognate pseudoviruses.

The results described in Example 3 are consistent with the idea that VP1 mutations observed in the CSF of PML patients could, in addition to altering viral tropism, confer a selective advantage to the virus by allowing escape from the apparently restricted spectrum of JCV-neutralizing antibodies (a neutralization "blind spot") observed in a small minority of individuals. To investigate the idea that the unusual phenotype of having JCV-neutralization blind spots might be associated with an increased risk of developing PML under conditions of immunodeficiency, neutralization serology was performed on a panel of plasma samples from PML patients. Two issues were considered in these experiments. First, PML patients might exhibit a narrow neutralization blind spot encompassing only the specific JCV VP1 sequence found in their CSF during PML. Second, neutralization blind spots might close during or after the development of PML. These considerations restricted the focus to patients for whom plasma samples had been collected and archived prior to the diagnosis of PML, and for whom the JCV sequences found in their CSF during PML were known. Six PML patients met these criteria.

Figure 6:
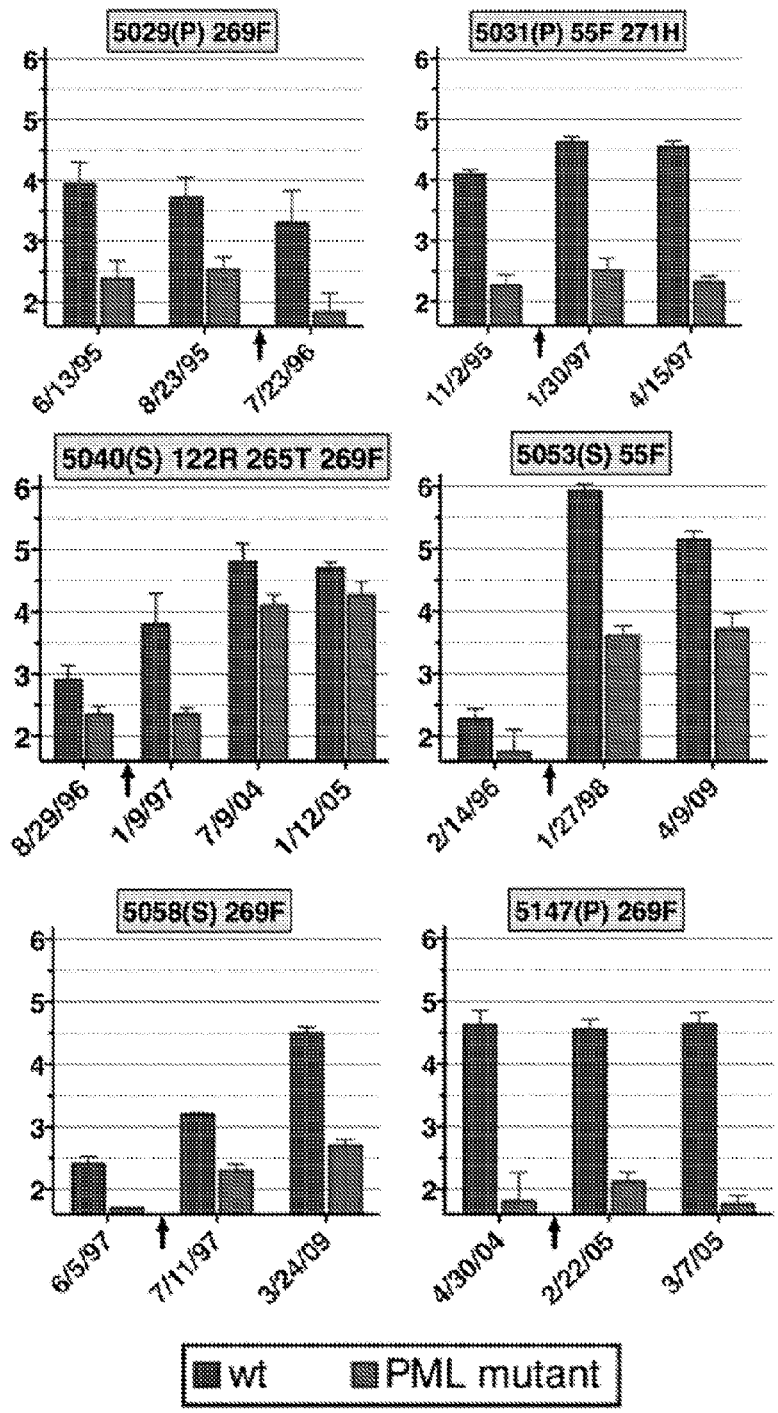

Pseudoviruses were constructed to represent the cognate mutant VP1 sequence found in individual patients' CSF during PML, together with the inferred wt VP1 sequence (Table 4). In some instances, serum samples were tested against near-cognate pseudoviruses. As shown in FIG. 6, all six patients exhibited little or no neutralization of cognate PML-mutant pseudoviruses at time points prior to PML diagnosis, even when there was robust neutralization of the wt patient-cognate (or wt 2A) pseudovirus. The results demonstrate that PML-specific VP1 mutations can allow the virus to escape from antibody-mediated neutralization.

Patients who survived PML eventually developed broader antibody responses capable of neutralizing their cognate PML-mutant pseudovirus. This suggests that at least some individuals with neutralization blind spots are ultimately capable of mounting broadly cross-neutralizing antibody responses. In contrast to patients who survived PML, the three patients with progressive (fatal) disease did not develop the ability to neutralize their cognate mutant virus. The results suggest a scenario in which the closing of humoral blind spots correlates with successful resolution of neuropathic JCV infection.

Figure 3:
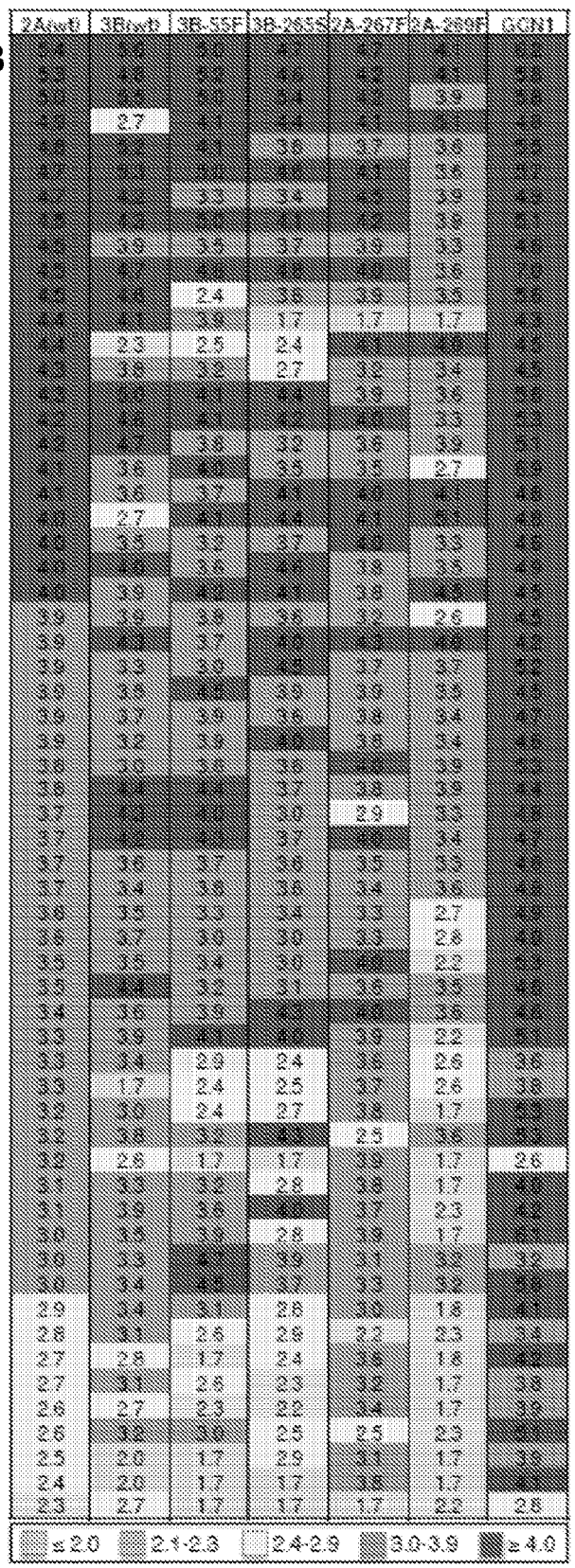
FIG. 3 is a diagram showing pseudovirus neutralization by sera from 60 healthy adult subjects. Data are presented as $\log_{10} EC_{50}$ values.
Figure 7:
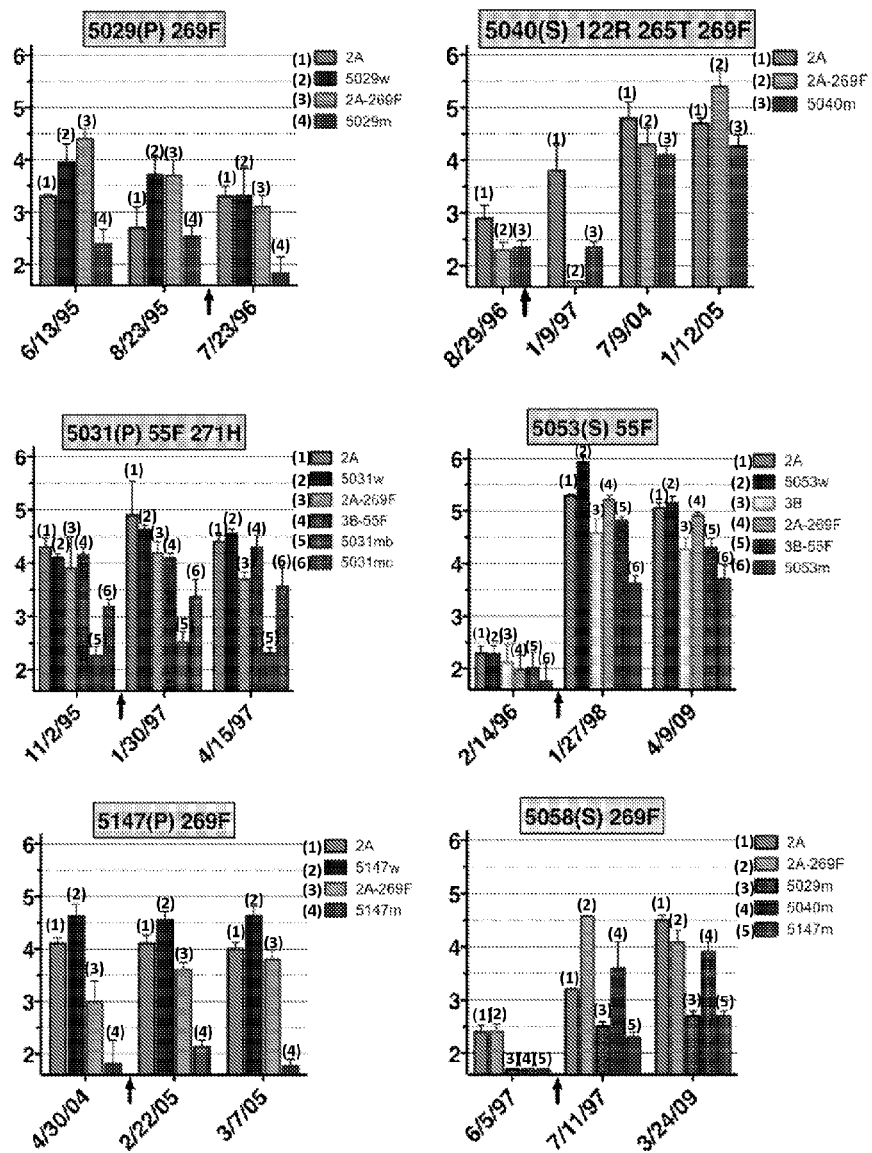

Remarkably, plasma from patients 5029 and 5058 robustly neutralized the 2A-269F pseudovirus at time points where poor neutralization of the patient-cognate-269F mutant virus was observed (FIG. 7), suggesting that naturally occurring variations outside the PML mutation "hotspots" can also influence neutralization-escape phenotypes. This is consistent with the observation that a few healthy subject sera that robustly neutralized the wt 2A pseudovirus showed very low titers against the wt 3B pseudovirus (FIG. 3). Taken together, the results illustrate the caveat that it is essential to analyze the neutralizability of the exact VP1 sequence(s) observed in any given subject.

Example 6

Treatment of a Patient with PML with JCV VP1 VLPs

This example describes treatment of a patient with PML by administration of JCV VP1 VLPs.

Figure 8:
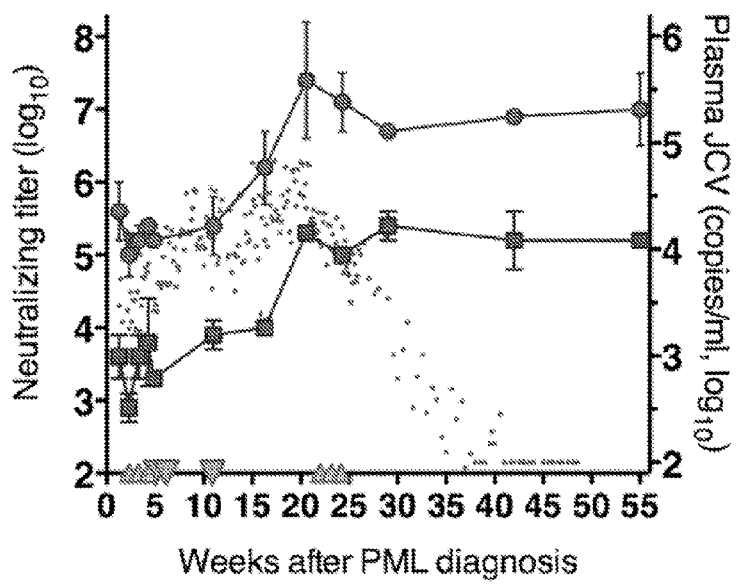
Figure 9:
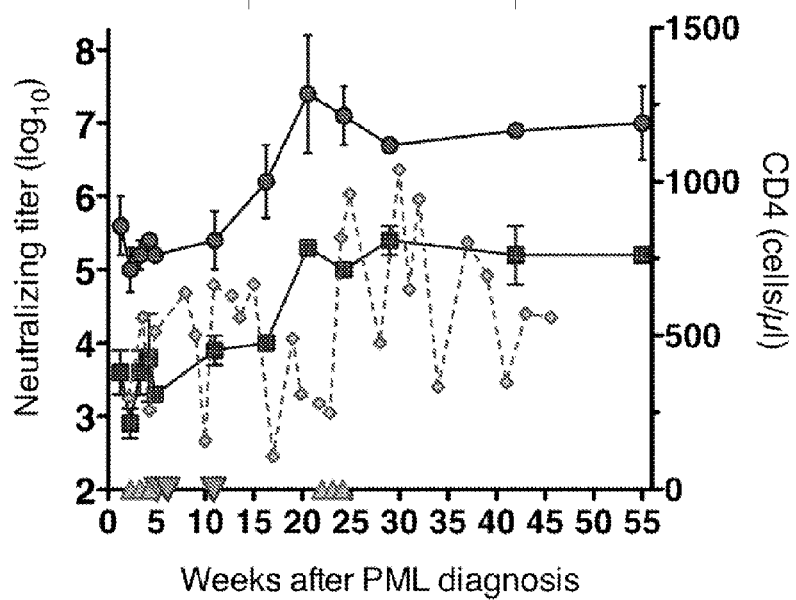

JCV genotype 1A VP1 VLP preparations suitable for compassionate use in PML patients have recently been developed (Sospedra et al., *Clin. Infect. Dis.* 59:1588-1592, 2014). PML patient 5228 is a 75 year-old female with idiopathic CD4 lymphopenia who was admitted at the Department of Infectious Diseases of San Raffaele Hospital, Milan, Italy upon diagnosis with PML. The patient's clinical condition deteriorated rapidly after admission and she became comatose. In addition to standard regimens of mefloquine and mirtazapine, the patient was treated with interleukin-7 (IL-7) and JCV VLPs. As shown in FIG. 8, vaccination was followed by a roughly 100-fold increase in the patient's neutralizing titer against her cognate mutant virus and a peak titer of 25 million against her inferred wt virus. This exceptionally high neutralizing titer is particularly remarkable in the sense that the patient was suffering from intermittent lymphopenia at the time of vaccination (FIG. 9).

The increases in JCV-neutralizing titer preceded a gradual fall in JCV viremia and an arrest of PML lesion progression.

Figures 10A, 10B, 10C:
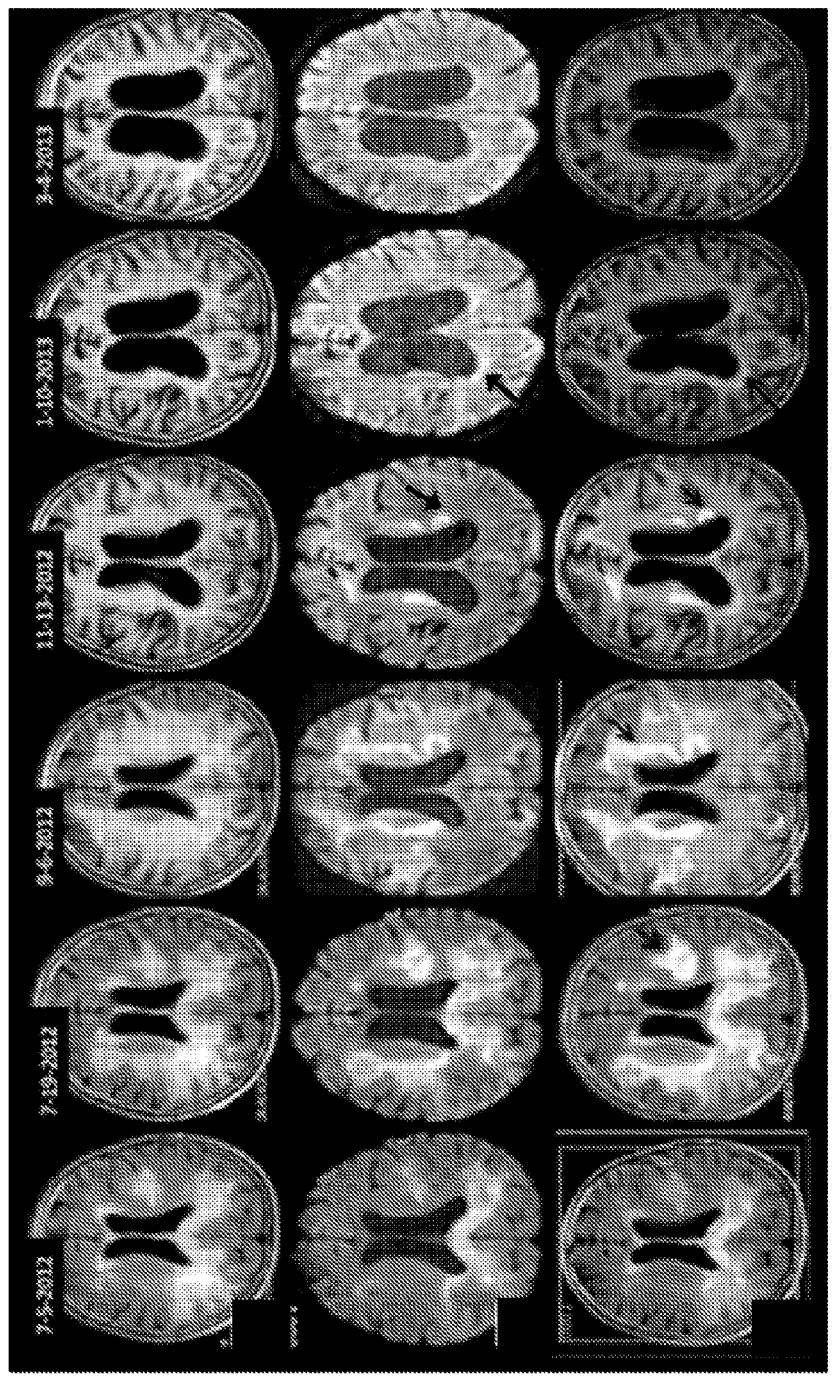

MRI lesions were active until about 8 months after presentation, but no activity was observed by MRI 11 months after presentation (FIG. 10). About three months after initial treatment CSF JCV-DNA increased to 95,430 c/ml, but decreased to low level on testing about six months later (2841 c/ml); no additional CSF examination was performed. Plasma JCV-DNA levels increased progressively and remained stable at high copy numbers until about four months after initial treatment, at which point levels began decreasing and ultimately became undetectable in about four months later (FIG. 8). The patient survived but remained comatose. There was no longer evidence of lesion activity at the last MRI about eight months after presentation with PML. JCV DNA remained undetectable in plasma at last examination, nearly two years after treatment was started.

Example 7

Methods of Eliciting an Immune Response to JCV

This example provides exemplary methods for eliciting an immune response to one or more JCV genotypes in a subject. However, one skilled in the art will appreciate that methods that deviate from these specific methods can also be used to successfully elicit an immune response to JCV in a subject.

In particular examples, the method includes selecting a subject in need of enhanced immunity to JCV. Subjects in need of enhanced immunity to JCV include individuals who are immunocompromised and individuals who have PML. Subjects in need of enhanced immunity to JCV also include individuals who are seronegative for at least one JCV genotype (including at least one PML-associated JCV genotype).

Subjects selected for treatment are administered a therapeutically effective amount of a disclosed immunogenic composition. In some examples, an effective amount of a JCV VP1 polypeptide with at least 99% identity to SEQ ID NO: 1, SEQ ID NO: 2, SEQ ID NO: 10, or SEQ ID NO: 27 is administered to the subject at doses of about 0.1 µg to 10 mg of the JCV VP1 polypeptide or about 0.1 µg to 10 mg of VLPs including a JCV polypeptide with at least 99% identity to SEQ ID NO: 1, SEQ ID NO: 2, SEQ ID NO: 10, or SEQ ID NO: 27 is administered to the subject. However, the particular dose can be determined by a skilled clinician. The disclosed JCV VP1 polypeptide or VLP is administered in one or several doses, for example at least two doses separated by one or more weeks.

The mode of administration can be any used in the art, including but not limited to subcutaneous or intramuscular administration. The amount of agent administered to the subject can be determined by a clinician, and may depend on the particular subject treated. Specific exemplary amounts are provided herein (but the disclosure is not limited to such doses).

The development of immune response (such as development of antibodies, such as neutralizing antibodies) in a subject is monitored at time points following administration of the immunogenic composition. Methods of detecting antibodies in a sample (such as a blood or serum sample) include those disclosed herein (e.g., in Example 1) as well as other methods known in the art, for example, ELISA methods.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of eliciting an immune response against a JC polyomavirus (JCV) in a subject, comprising administering to the subject an effective amount of an immunogenic composition comprising an isolated JCV genotype 2 VP1 polypeptide, an isolated JCV genotype 3 VP1 polypeptide, or a combination thereof, or an isolated nucleic acid encoding the VP1 polypeptide(s), thereby eliciting an immune response to JCV.

2. The method of claim 1, wherein the immunogenic composition consists essentially of the isolated JCV genotype 2 VP1 polypeptide, the isolated JCV genotype 3 VP1 polypeptide, or a combination thereof, or the isolated nucleic acid encoding the VP1 polypeptide.

3. A method of eliciting an immune response against a JC polyomavirus (JCV) in a subject, comprising administering to the subject an effective amount of a monovalent immunogenic composition comprising an isolated JCV genotype 2 or JCV genotype 3 VP1 polypeptide or an isolated nucleic acid encoding the VP1 polypeptide, thereby eliciting an immune response to JCV.

4. The method of claim 1, wherein the JCV genotype 2 VP1 polypeptide comprises a JCV genotype 2A VP1 polypeptide or the JCV genotype 3 VP1 polypeptide comprises a JCV genotype 3B VP1 polypeptide.

5. The method of claim 1, wherein the JCV VP1 polypeptide comprises an amino acid sequence having at least 99% identity to the amino acid sequence set forth as SEQ ID NO: 1, SEQ ID NO: 2, or SEQ ID NO: 9.

6. The method of claim 1, wherein the JCV VP1 polypeptide comprises or consists of the amino acid sequence set forth as SEQ ID NO: 1, SEQ ID NO: 2, or SEQ ID NO: 9.

7. The method of claim 1, wherein the nucleic acid encoding the VP1 polypeptide comprises the nucleic acid sequence set forth as any one of SEQ ID NOs: 16-18, 25, or 26.

8. The method of claim 1, wherein administering the immunogenic composition comprising the isolated JCV genotype 2 VP1 polypeptide, the isolated JCV genotype 3 VP1 polypeptide, or both, comprises administering a virus-like particle comprising the VP1 polypeptide.

9. The method of claim 1, wherein eliciting the immune response to JCV comprises eliciting a neutralizing antibody response.

10. The method of claim 9, wherein the neutralizing antibody response neutralizes two or more JCV genotypes.

11. The method of claim 9, wherein the immune response neutralizes JCV comprising a wild type or a variant VP1 polypeptide.

12. The method of claim 9, wherein the neutralizing antibody response neutralizes one or more JCVs comprising a variant VP1 polypeptide.

13. The method of claim 1, further comprising administering an adjuvant to the subject.

14. The method of claim 13, wherein the adjuvant comprises alum.

15. The method of claim 1, wherein the subject is an immunocompromised subject, a subject who has been treated with or is a candidate for treatment with an immunosuppressant, a subject who has received or is a candidate for an organ transplant or bone marrow transplant, or a subject with progressive multifocal leukoencephalopathy.

16. The method of claim 1, wherein the subject does not have JCV neutralizing antibodies.

17. A method of identifying a subject at risk of developing progressive multifocal leukoencephalopathy (PML), comprising:
obtaining a biological sample from the subject;
detecting presence or absence of detectable JC polyomavirus (JCV) neutralizing antibodies in the sample from the subject;
identifying the subject as being at risk of developing PML if there is absence of detectable JCV neutralizing antibodies in the sample from the subject; and
administering an effective amount of an immunogenic composition comprising an isolated JCV VP1 polypeptide or an isolated nucleic acid encoding the VP1 polypeptide to the subject identified as being at risk of developing PML.

18. The method of claim 17, wherein the subject is an immunocompromised subject, a subject who has been treated with or is a candidate for treatment with an immunosuppressant, or a subject who has received or is a candidate for an organ transplant or bone marrow transplant.

19. The method of claim 17, wherein the biological sample from the subject comprises a blood sample or a serum sample.

20. The method of claim 17, wherein the JCV VP1 polypeptide comprises a JCV genotype 2 VP1 polypeptide, a JCV genotype 3 VP1 polypeptide, or a combination thereof.

21. An immunogenic composition comprising:
(a) an isolated JCV genotype 2 VP1 polypeptide, an isolated JCV genotype 3 VP1 polypeptide, or a combination thereof, or a nucleic acid encoding the VP1 polypeptide(s); and
(b) an adjuvant.

22. The immunogenic composition of claim 21, wherein the JCV genotype 2 VP1 polypeptide comprises a JCV genotype 2A VP1 polypeptide or the JCV genotype 3 VP1 polypeptide comprises a JCV genotype 3B VP1 polypeptide.

23. The immunogenic composition of claim 21, wherein the adjuvant comprises aluminum hydroxide, aluminum phosphate, or a combination thereof.

24. The immunogenic composition of claim 21, further comprising a sterile pharmaceutically acceptable carrier.

25. The immunogenic composition of claim 21, wherein the isolated JCV VP1 polypeptide comprises an amino acid sequence having at least 99% identity to the amino acid sequence set forth as SEQ ID NO: 1, SEQ ID NO: 2, or SEQ ID NO: 9.

26. The immunogenic composition of claim 25, wherein the isolated JCV VP1 polypeptide comprises or consists of the amino acid sequence set forth as SEQ ID NO: 1, SEQ ID NO: 2, or SEQ ID NO: 9.

27. The immunogenic composition of claim 21, wherein the nucleic acid encoding the VP1 polypeptide comprises the nucleic acid sequence set forth as any one of SEQ ID NOs: 16-18, 25, or 26.

28. A method of eliciting in a subject a neutralizing antibody response to a JCV VP1 variant polypeptide, comprising administering to the subject an effective amount of an immunogenic composition comprising an isolated wild type JCV genotype 1A VP1 polypeptide, an isolated wild type JCV genotype 2A VP1 polypeptide, an isolated wild type JCV genotype 3B VP1 polypeptide, or a combination thereof, or an isolated nucleic acid encoding the VP1 polypeptide(s), thereby eliciting a neutralizing antibody response to a JCV VP1 variant polypeptide.

29. The method of claim 28, wherein the wild type JCV genotype 1A VP1 polypeptide comprises the amino acid sequence of SEQ ID NOs: 10 or 27, the wild type JCV genotype 2A VP1 polypeptide comprises the amino acid sequence of SEQ ID NOs: 1 or 9, or the wild type JCV genotype 3B VP1 polypeptide comprises the amino acid sequence of SEQ ID NO: 2.

30. The method of claim 28, wherein administering the immunogenic composition comprising the isolated JCV genotype 2A VP1 polypeptide, the isolated JCV genotype 2A VP1 polypeptide, or the isolated JCV genotype 3B VP1 polypeptide comprises administering a virus-like particle comprising the VP1 polypeptide.

31. The immunogenic composition of claim 21, wherein the JCV genotype 2 VP1 polypeptide, the JCV genotype 3 VP1 polypeptide, or a combination thereof is included in a virus-like particle.

* * * * *

SEQUENCE LISTING

```
<160> NUMBER OF SEQ ID NOS: 27

<210> SEQ ID NO 1
<211> LENGTH: 354
<212> TYPE: PRT
<213> ORGANISM: JC virus

<400> SEQUENCE: 1

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125
```

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 2
<211> LENGTH: 354
<212> TYPE: PRT
<213> ORGANISM: JC virus

<400> SEQUENCE: 2

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Ala Lys Pro Val Gln Gly Thr Ser Phe His Phe
    130                 135                 140

```
Phe Ser Val Gly Gly Glu Ala Leu Glu Leu Gln Gly Val Val Phe Asn
145                 150                 155                 160

Tyr Arg Thr Thr Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Ile Glu Glu Val Arg Val Phe Glu Gly Thr Glu Gln Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 3
<211> LENGTH: 354
<212> TYPE: PRT
<213> ORGANISM: JC virus

<400> SEQUENCE: 3

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Phe Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Ala Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160
```

-continued

```
Tyr Arg Thr Thr Tyr Pro Asp Gly Thr Ile Phe Pro Lys Asn Ala Thr
            165                 170                 175

Val Gln Ser Gln Val Met Asn Thr Glu His Lys Ala Tyr Leu Asp Lys
        180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
            245                 250                 255

Val Asp Val Cys Gly Met Phe Thr Asn Arg Ser Gly Ser Gln Gln Trp
        260                 265                 270

Arg Gly Leu Ser Arg Tyr Phe Lys Val Gln Leu Arg Lys Arg Arg Val
    275                 280                 285

Lys Asn Pro Tyr Pro Ile Ser Phe Leu Leu Thr Asp Leu Ile Asn Arg
        290                 295                 300

Arg Thr Pro Arg Val Asp Gly Gln Pro Met Tyr Gly Met Asp Ala Gln
305                 310                 315                 320

Ile Glu Glu Val Arg Val Phe Glu Gly Thr Glu Gln Leu Pro Gly Asp
            325                 330                 335

Pro Asp Met Met Arg Tyr Val Asp Arg Tyr Gly Gln Leu Gln Thr Lys
        340                 345                 350

Met Leu

<210> SEQ ID NO 4
<211> LENGTH: 354
<212> TYPE: PRT
<213> ORGANISM: JC virus

<400> SEQUENCE: 4

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Phe Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
            85                  90                  95

Cys Gly Asn Ile Leu Met Trp Glu Ala Val Thr Leu Lys Thr Glu Val
        100                 105                 110

Ile Gly Val Thr Thr Leu Met Asn Val His Ser Asn Gly Gln Ala Thr
    115                 120                 125

His Asp Asn Gly Ala Ala Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Thr Tyr Pro Asp Gly Thr Ile Phe Pro Lys Asn Ala Thr
            165                 170                 175
```

```
Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Ser Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Ile Glu Glu Val Arg Val Phe Glu Gly Thr Glu Gln Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 5
<211> LENGTH: 354
<212> TYPE: PRT
<213> ORGANISM: JC virus

<400> SEQUENCE: 5

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190
```

-continued

```
Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Phe Gly Ser Gln His Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 6
<211> LENGTH: 354
<212> TYPE: PRT
<213> ORGANISM: JC virus

<400> SEQUENCE: 6

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
        50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Ala Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Thr Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205
```

-continued

```
Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Phe Gly Ser Gln His Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Ile Glu Glu Val Arg Val Phe Glu Gly Thr Glu Gln Leu Pro Gly Asp
                325                 330                 335

Pro Asp Met Met Arg Tyr Val Asp Arg Tyr Gly Gln Leu Gln Thr Lys
            340                 345                 350

Met Leu
```

<210> SEQ ID NO 7
<211> LENGTH: 354
<212> TYPE: PRT
<213> ORGANISM: JC virus

<400> SEQUENCE: 7

```
Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220
```

```
Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
            245                 250                 255

Val Asp Val Cys Gly Met Phe Thr Asn Arg Ser Gly Phe Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 8
<211> LENGTH: 354
<212> TYPE: PRT
<213> ORGANISM: JC virus

<400> SEQUENCE: 8

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Phe Arg Gly Phe Ser Lys Ser Ile Ser Ile
50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Ala Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Thr Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240
```

-continued

```
Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Lys Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Ile Glu Glu Val Arg Val Phe Glu Gly Thr Glu Gln Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 9
<211> LENGTH: 345
<212> TYPE: PRT
<213> ORGANISM: JC virus

<400> SEQUENCE: 9

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
        50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Gly Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255
```

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
        290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg
            340                 345

<210> SEQ ID NO 10
<211> LENGTH: 354
<212> TYPE: PRT
<213> ORGANISM: JC virus

<400> SEQUENCE: 10

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Leu Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

```
Lys Asn Pro Tyr Pro Ile Ser Phe Leu Leu Thr Asp Leu Ile Asn Arg
        290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Lys Tyr Gly Gln Leu Gln Thr Lys
            340                 345                 350

Met Leu

<210> SEQ ID NO 11
<211> LENGTH: 354
<212> TYPE: PRT
<213> ORGANISM: JC virus

<400> SEQUENCE: 11

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Val
    50                  55                  60

Ser Asp Thr Phe Glu Ser Asp Ser Pro Ser Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Ala
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Ser Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300
```

```
Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
            325                 330                 335

Pro Asp Met Met Arg Tyr Val Asp Arg Tyr Gly Gln Leu Gln Thr Lys
        340                 345                 350

Met Leu

<210> SEQ ID NO 12
<211> LENGTH: 354
<212> TYPE: PRT
<213> ORGANISM: JC virus

<400> SEQUENCE: 12

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Val Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Ala Lys Pro Val Gln Gly Thr Ser Phe His Phe
    130                 135                 140

Phe Ser Val Gly Gly Glu Ala Leu Glu Leu Gln Gly Val Ala Phe Asn
145                 150                 155                 160

Tyr Arg Thr Thr Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Val Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320
```

```
Val Glu Glu Val Arg Val Phe Glu Gly Thr Glu Leu Pro Glu Asp
            325                 330                 335

Pro Asp Met Met Arg Tyr Val Asp Arg Tyr Gly Gln Leu Gln Thr Lys
            340                 345                 350

Met Leu

<210> SEQ ID NO 13
<211> LENGTH: 354
<212> TYPE: PRT
<213> ORGANISM: JC virus

<400> SEQUENCE: 13

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
            115                 120                 125

His Asp Asn Gly Ala Gly Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Thr Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
                325                 330                 335
```

Pro Asp Met Met Arg Tyr Val Asp Arg Tyr Gly Gln Leu Gln Thr Lys
            340                 345                 350
Met Leu

<210> SEQ ID NO 14
<211> LENGTH: 354
<212> TYPE: PRT
<213> ORGANISM: JC virus

<400> SEQUENCE: 14

Met Ala Pro Thr Lys Arg Lys Gly Glu Arg Lys Asp Pro Val Gln Val
1               5                   10                  15
Pro Lys Leu Leu Ile Arg Gly Gly Val Glu Val Leu Glu Val Lys Thr
            20                  25                  30
Gly Val Asp Ser Ile Thr Glu Val Glu Cys Phe Leu Thr Pro Glu Met
        35                  40                  45
Gly Asp Pro Asp Glu His Leu Arg Gly Phe Ser Lys Ser Ile Ser Ile
    50                  55                  60
Ser Asp Thr Phe Glu Ser Asp Ser Pro Asn Lys Asp Met Leu Pro Cys
65                  70                  75                  80
Tyr Ser Val Ala Arg Ile Pro Leu Pro Asn Leu Asn Glu Asp Leu Thr
                85                  90                  95
Cys Gly Asn Ile Leu Met Trp Glu Ala Val Thr Leu Lys Thr Glu Val
            100                 105                 110
Leu Gly Val Thr Thr Leu Met Asn Val His Ser Asn Gly Gln Ala Thr
        115                 120                 125
His Asp Asn Gly Ala Gly Lys Pro Val Gln Gly Thr Ser Phe His Phe
    130                 135                 140
Phe Ser Val Gly Gly Glu Ala Leu Glu Leu Gln Gly Val Val Phe Asn
145                 150                 155                 160
Tyr Arg Thr Lys Tyr Pro Asp Gly Thr Ile Phe Pro Lys Asn Ala Thr
                165                 170                 175
Val Gln Ser Gln Val Met Asn Thr Glu His Lys Ala Tyr Leu Asp Lys
            180                 185                 190
Asn Lys Ala Tyr Pro Val Glu Cys Trp Val Pro Asp Pro Thr Arg Asn
        195                 200                 205
Glu Asn Thr Arg Tyr Phe Gly Thr Leu Thr Gly Gly Glu Asn Val Pro
    210                 215                 220
Pro Val Leu His Ile Thr Asn Thr Ala Thr Thr Val Leu Leu Asp Glu
225                 230                 235                 240
Phe Gly Val Gly Pro Leu Cys Lys Gly Asp Asn Leu Tyr Leu Ser Ala
                245                 250                 255
Val Asp Val Cys Gly Met Phe Thr Asn Arg Ser Gly Ser Gln Gln Trp
            260                 265                 270
Arg Gly Leu Ser Arg Tyr Phe Lys Val Gln Leu Arg Lys Arg Arg Val
        275                 280                 285
Lys Asn Pro Tyr Pro Ile Ser Phe Leu Leu Thr Asp Leu Ile Asn Arg
    290                 295                 300
Arg Thr Pro Lys Val Asp Gly Gln Pro Met Tyr Gly Met Asp Ala Gln
305                 310                 315                 320
Ile Glu Glu Val Arg Val Phe Glu Gly Thr Glu Glu Leu Pro Gly Asp
                325                 330                 335
Pro Asp Met Met Arg Tyr Val Asp Arg Tyr Gly Gln Leu Gln Thr Lys
            340                 345                 350

Met Leu

<210> SEQ ID NO 15
<211> LENGTH: 354
<212> TYPE: PRT
<213> ORGANISM: JC virus

<400> SEQUENCE: 15

```
Met Ala Pro Thr Lys Arg Lys Gly Glu Arg Lys His Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Thr Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu
```

<210> SEQ ID NO 16
<211> LENGTH: 1065
<212> TYPE: DNA
<213> ORGANISM: JC virus

<400> SEQUENCE: 16

```
atggccccaa caaaaagaaa aggagaaagg aaggaccccg tgcaagttcc aaaacttctt      60
ataagaggag gagtagaagt tctagaagtt aaaactgggg ttgactcaat tacagaggta     120
gaatgttttt taactccaga aatgggtgac ccagatgagc atcttagggg ttttagtaag     180
tcaatttcta tatcagatac atttgaaagt gactccccaa ataaggacat gcttccttgt     240
tacagtgtgg ccagaattcc actacccaat ctaaatgagg atctaacctg tggaaatata     300
ctaatgtggg aggctgtgac cttaaaaact gaggttatag ggtaacaac tttgatgaat      360 gtgcactcta atggtcaagc aactcatgac aatggtgcag gaaagccagt gcagggcacc     420
agctttcatt ttttttctgt tggggggag gctttagaat tacaggggt ggttttaac       480 tacagaacaa agtacccaga tggaacaatt tttccaaaga atgcaacagt gcaatctcaa     540
gtaatgaaca cagagcacaa ggcgtaccta gataagaaca aagcatatcc tgttgaatgt     600
tgggttcctg atcccaccag aaatgaaaac acaagatatt tgggacact aacaggagga     660 gaaaatgttc ctccagttct tcatataaca aacactgcca caacagtgct gcttgatgaa     720
tttggtgttg ggccactttg caaaggtgac aacttgtatt tgtcagctgt ggatgtttgt     780 ggcatgtta ctaacagatc tggttcccag cagtggagag gactgtccag atatttttaag    840 gttcagctaa gaaaaaggag ggttaaaaac ccctacccaa tttctttcct tcttactgat     900
ttaattaaca gaaggacccc tagagttgat gggcagccta tgtatggcat ggatgctcag     960 gtagaggag ttagagtttt tgaggggaca gaggaacttc caggggaccc cagacatgatg   1020 agatatgttg acagatatgg acagttgcaa acaaagatgc tgtaa                   1065
```

<210> SEQ ID NO 17
<211> LENGTH: 1065
<212> TYPE: DNA
<213> ORGANISM: JC virus

<400> SEQUENCE: 17

```
atggccccaa caaaaagaaa aggagaaagg aaggaccccg tgcaagttcc aaaacttctt      60
ataagaggag gagtagaagt tctagaagtt aaaactgggg ttgactcaat tacagaggta     120
gaatgctttt taactccaga aatgggtgac ccagatgagc atcttagggg ttttagtaag     180
tcaatttcta tatcagatac atttgaaagt gactccccaa ataaggacat gcttccttgt     240
tacagtgtgg ccagaattcc actacccaat ctaaatgagg atcttacctg tggaaatata     300
ctaatgtggg aggctgtaac cttaaaaact gaggtcatag ggtgacaac tttgatgaat     360 gtgcactcta atggtcaagc aactcatgac aatggtgcag caaagccagt gcagggcacc     420
agctttcatt ttttttctgt tggggggag gctttagaat tacaggggt ggttttaat      480 tacagaacaa cgtacccaga tggaacaatt tttccaaaga atgcaacagt gcaatctcaa     540
gtaatgaaca cagagcacaa ggcgtaccta gataagaaca aagcatatcc tgttgaatgt     600
tgggttcctg atcccaccag aaatgaaaac acaagatatt tgggacact aacaggagga     660 gaaaatgttc ctccagttct tcatataaca aacactgcca caacagtgct gcttgatgaa     720
tttggtgttg ggccactttg caaaggtgac aacttgtatt tgtcagctgt tgatgtttgt     780 ggcatgtta ctaacagatc tggttcccag cagtggagag gactctccag atatttttaag    840
```

```
gttcagctaa gaaaaaggag ggttaaaaac ccctacccaa tttctttcct tcttactgac    900
ttaattaaca gaaggacccc tagagttgat gggcagccta tgtatggcat ggatgctcaa    960
atagaggagg ttagagtttt tgaggggaca gagcaacttc caggggaccc agatatgatg   1020
agatatgttg acagatatgg acagttgcag acaaaaatgc tgtaa                   1065
```

<210> SEQ ID NO 18
<211> LENGTH: 1034
<212> TYPE: DNA
<213> ORGANISM: JC virus

<400> SEQUENCE: 18

```
atggcccca acaaaagaaa aggagaaagg aaggaccccg tgcaagttcc aaaacttctt     60
ataagaggag gagtagaagt tctagaagtt aaaactgggg ttgactcaat tacagaggta    120
gaatgctttt taactccaga aatgggtgac ccagatgagc atcttagggg ttttagtaag    180
tcaatttcta tatcagatac atttgaaagt gactccccaa ataaggacat gcttccttgt    240
tacagtgtgg ccagaattcc actacccaat ctaaatgagg atcttacctg tggaaatata    300
ctaatgtggg aggctgtgac cttaaaaact gaggtcatag gggtgacaac tttgatgaat    360
gtgcactcta atggtcaagc aactcatgac aatggtgcag caaagccagt gcagggcacc    420
agctttcatt ttttttctgt tgggggggag gctttagaat tacaggggt ggttttttaat    480 tacagaacaa cgtacccaga tggaacaatt tttccaaaga atgcaacagt gcaatctcaa    540
gtaatgaaca cagagcacaa ggcgtaccta gataagaaca aagcatatcc tgttgaatgt    600
tgggttcctg atcccaccag aaatgaaaac acaagatatt ttgggacact aacaggagga    660
gaaaatgttc ctccagttct tcatataaca acactgcca caacagtgct gcttgatgaa    720
tttggtgttg gccactttg caaggtgac aacttgtatt tgtcagctgt tgatgttgt    780 ggcatgttta ctaacagatc tggttcccag cagtggagag gactctccag atatttaag    840 gttcagctaa gaaaaaggag ggttaaaaac ccctacccaa tttctttcct tcttactgat    900
ttaattaaca gaaggacccc tagagttgat gggcagccta tgtatggtat ggatgctcaa    960
atagaggagg ttagagtttt tgaggggaca gagcaacttc caggagaccc agatatgatg   1020
agatatgttg acag                                                     1034
```

<210> SEQ ID NO 19
<211> LENGTH: 1065
<212> TYPE: DNA
<213> ORGANISM: JC virus

<400> SEQUENCE: 19

```
atggcccca acaaaagaaa aggagaaagg aaggaccccg tgcaagttcc aaaacttctt     60
ataagaggag gagtagaagt tctagaagtt aaaactgggg ttgactcaat tacagaggta    120
gaatgctttt taactccaga aatgggtgac ccagatgagc atcttagggg ttttagtaag    180
tcaatatcta tatcagatac atttgaaagt gactccccaa ataaggacat gcttccttgt    240
tacagtgtgg ccagaattcc actacccaat ctaaatgagg atctaacctg tggaaatata    300
ctcatgtggg aggctgtgac cttaaaaact gaggttatag gggtgacaag tttgatgaat    360
gtgcactcta atgggcaagc aactcatgac aatggtgcag ggaagccagt gcagggcacc    420
agctttcatt ttttttctgt tgggggggag gctttagaat tacaggggt gcttttttaat    480 tacagaacaa agtacccaga tggaacaatt tttccaaaga atgccacagt gcaatctcaa    540
```

```
gtcatgaaca cagagcacaa ggcgtaccta gataagaaca aagcatatcc tgttgaatgt      600
tgggttcctg atcccaccag aaatgaaaac acaagatatt tgggacact aacaggagga      660 gaaaatgttc ctccagttct tcatataaca acactgcca caacagtgtt gcttgatgaa      720
tttggtgttg ggccactttg caaaggtgac aacttatact tgtcagctgt tgatgtctgt      780
ggcatgttta ctaacaggtc aggttcccag cagtggagag gactctccag atattttaag      840
gttcagctaa ggaaaaggag ggttaaaaac ccctacccaa tttcttttcct tcttactgat     900 ctaattaaca gaaggactcc tagagttgat gggcagccta tgtatggcat ggatgctcaa      960
gttgaggagg ttagagtttt tgagggaaca gaggagcttc caggggaccc agacatgatg     1020
agatatgttg acaaatatgg acagttgcag acaaaaatgc tgtaa                     1065
```

<210> SEQ ID NO 20
<211> LENGTH: 1065
<212> TYPE: DNA
<213> ORGANISM: JC virus

<400> SEQUENCE: 20

```
atggccccaa caaaaagaaa aggagaaagg aaggaccccg tgcaagttcc aaaacttctt       60
ataagaggag gagtagaagt tctagaagtt aaaactgggg ttgactcaat tacagaggta      120
gaatgctttt taactccaga aatgggtgac ccagatgagc atcttagggg ttttagtaag      180
tcaatatctg tatcagatac atttgaaagt gactccccaa gtaaggacat gcttccttgt      240
tacagtgtgg ccagaattcc actacccaat ctaaatgagg atctaacctg tggaaatata      300
ctcatgtggg aggctgtgac cttaaaaact gaggttatag gggtgacaag tttgatgaat      360
gtgcactcta atggtcaagc agctcatgac aatggtgcag ggaagccagt gcagggcacc      420
agctttcatt ttttttctgt tggggggag gctttagaat tacaggggt ggttttaat        480 tacagaacta agtacccaga tggaacaatt tttccaaaga atgccacagt gcaatctcaa      540
gtcatgaaca cagagcacaa ggcgtaccta gataagaaca aagcatatcc tgttgaatgt      600
tgggttcctg atcccaccag aaatgaaaac acaagatatt tgggacact aacaggagga      660 gaaagtgttc ctccagttct tcatataaca acactgcca caacagtgtt gcttgatgaa      720
tttggtgttg ggccactttg caaaggtgac aacttatact tgtcagctgt tgatgtctgt      780
ggcatgttta ctaacaggtc tggttcccag cagtggagag gactctccag atattttaag      840
gttcagctaa ggaaaaggag ggttaaaaac ccctacccaa tttcttttcct tcttactgat     900 ttaattaaca gaaggactcc tagagttgat gggcagccta tgtatggcat ggatgctcaa      960
gtagaggagg ttagagtttt tgagggaaca gaggagcttc caggggaccc agacatgatg     1020
agatacgttg acagatatgg acagttgcag acaaaaatgc tgtaa                     1065
```

<210> SEQ ID NO 21
<211> LENGTH: 1065
<212> TYPE: DNA
<213> ORGANISM: JC virus

<400> SEQUENCE: 21

```
atggccccaa caaaaagaaa aggagaaagg aaggaccccg tgcaagttcc aaaacttctt       60
ataagaggag gagtagaagt tctagaagtt aaaactgggg ttgactcaat tacagaggta      120
gaatgctttt taactccaga aatgggtgac ccagatgagc atcttagggg ttttagtaag      180
tctatatcta tatcagatac atttgaaagt gactccccaa ataaggacat gcttccttgt      240
tacagtgtgg ccagagttcc actacccaat ctaaatgagg atctaacctg tggaaatata      300
```

```
ctcatgtggg aggctgtgac cttaaaaact gaggttatag gggtgacaac tttgatgaat      360
gtgcactcta atgggcaagc aactcatgac aatggtgcag caaagccagt gcagggcacc      420
agctttcatt tttttctgt tggggggag gctttagaat tacagggggt ggcttttaat      480
tacagaacaa cgtacccaga tgaacaatt tttccaaaga atgccacagt gcaatctcaa      540
gtcatgaaca cagagcacaa ggcgtaccta gataagaaca agtatatcc tgttaatgt       600 tgggttcctg atcccaccag aaatgaaaac acaagatatt tgggacact aacaggagga     660 gaaaatgttc ctccagttct tcatataaca aacactgcca caacagtgtt gcttgatgaa     720
tttggtgttg ggccactttg caaaggtgac aacttatatt tgtcagctgt tgatgtctgt     780
ggcatgttta ctaacaggtc tggttcccag cagtggagag gactctccag atatttaag     840 gttcagctaa ggaaaaggag ggttaaaaac ccctacccaa tttctttct tcttactgat    900 ttaattaata gaaggactcc tagagttgat gggcagccta tgtatggcat ggatgctcaa    960
gtagaggagg ttagagtttt tgagggaaca gaggagcttc cagaggaccc agacatgatg    1020
agatacgttg acagatatgg acagttgcag acaaaaatgc tgtaa                     1065

<210> SEQ ID NO 22
<211> LENGTH: 1065
<212> TYPE: DNA
<213> ORGANISM: JC virus

<400> SEQUENCE: 22
atggccccaa caaaaagaaa aggagaaagg aaggaccccg tgcaagttcc aaaactactt      60
ataagaggag gagtagaagt tctagaagtt aaaactgggg ttgactcaat tacagaggta    120
gaatgctttt taactccaga aatgggtgac ccagatgagc attttagagg ttttagtaag    180
tcaatttcta tatcagatac atttgaaagt gactccccaa ataaggacat gcttccttgt    240
tacagtgtgg ccagaattcc actacccaat ctaaatgagg atctaacctg tggaaatata    300
ctaatgtggg aggctgtgac cctaaaaact gaggttatag gggtgacaac tttgatgaat    360
gtgcactcta atggtcaagc aactcatgac aatggtgcag gaagccagt gcagggcacc     420 agctttcatt tttttctgt tggggggag gctttagaat tacaagggggt ggtgttcaat    480 tacagaacaa cgtacccaga tgaacaatt tttccaaaga atgcaacagt gcagtctcaa    540
gtaatgaaca cagagcacaa ggcgtaccta gataagaaca agcatatcc tgttaatgt     600 tgggttcctg atcccaccag aaatgaaaac acaagatatt tgggacact aacaggagga    660 gaaaatgtgc ctccagttct tcatataaca aacactgcca caacagtgct gcttgatgaa    720
tttggtgttg ggccactttg caaaggtgac aacttgtatt tgtcagctgt tgatgtttgt    780
ggcatgttta ctaacagatc tggttcccag cagtggagag gactctccag atatttaag    840 gttcagctaa ggaaaaggag ggttaaaaac ccctacccaa tttctttcct tctgactgat    900
ttaatcaaca gaaggactcc tagagttgat gggcagccta tgtatggcat ggatgctcaa    960
gtagaggagg ttagagtttt tgaggggaca gaggaacttc caggggaccc agacatgatg    1020
agatatgttg acagatatgg acagttgcag accaaaatgc tgtaa                     1065

<210> SEQ ID NO 23
<211> LENGTH: 1065
<212> TYPE: DNA
<213> ORGANISM: JC virus

<400> SEQUENCE: 23
```

```
atggccccaa caaaaagaaa aggagaaagg aaggaccccg tgcaagttcc aaaacttctt    60
ataagaggag gagtagaagt tctagaagtt aaaactgggg ttgactcaat tacagaggta   120
gaatgctttt taactccaga aatgggtgac ccagatgagc atcttagggg ttttagtaag   180
tcaatttcta tatcagatac atttgaaagt gactccccaa ataaggacat gcttccttgt   240
tacagtgtgg ccagaattcc actacccaat ctaaatgagg atctaacctg tggaaatata   300
ctaatgtggg aggctgtgac cttaaagact gaggttttag gggtgacaac tttgatgaat   360
gtgcactcta atggtcaagc aactcatgac aatggtgcag gaaagccagt gcagggcacc   420
agctttcatt tttttctgt tggggggag gctttagaat tacaggggt ggtttttaat      480
tacagaacaa agtacccaga tggaacaatt tttccaaaga atgcaacagt gcaatctcaa   540
gtaatgaaca cagagcacaa ggcgtaccta gataagaaca aagcatatcc tgttgaatgt   600
tgggttcctg atcccaccag aaatgaaaac acaagatatt ttgggacact aacaggagga   660
gaaaatgttc ctccagttct tcatataaca aacactgcca caacagtgct gcttgatgaa   720
tttggtgttg ggccactttg caaaggtgac aacttgtatt tgtcagctgt tgatgtttgt   780
ggcatgttta ctaacagatc tggttcccag cagtggagag gactgtccag atattttaag   840
gttcagctaa gaaaaaggag ggttaaaaac ccctacccaa tttctttcct tcttactgat   900
ttaattaaca gaaggacccc taaagttgat gggcagccta tgtatggcat ggatgctcaa   960
atagaggagg ttagagtttt tgaggggaca gaggaactcc caggggaccc agacatgatg  1020
agatatgttg acagatatgg acagttgcag acaaaaatgc tgtaa                  1065
```

<210> SEQ ID NO 24
<211> LENGTH: 1065
<212> TYPE: DNA
<213> ORGANISM: JC virus

<400> SEQUENCE: 24

```
atggccccaa caaaaagaaa aggagaaagg aagcaccccg tgcaagttcc aaaacttctt    60
ataagaggag gagtagaagt tctagaagtt aaaactgggg ttgactcaat tacagaggta   120
gaatgctttt taactccaga aatgggtgac ccagatgagc atcttagggg ttttagtaag   180
tcaatttcca tatcagatac atttgaaagt gactccccaa ataaggacat gcttccttgt   240
tacagtgtgg ccagaattcc actacccaat ctaaatgagg atctaacctg tggaaatata   300
ctgatgtggg aggctgtgac cctaaaaact gaggttatag gggtgacaac tttgatgaat   360
gtgcactcta atggtcaagc aactcatgac aatggtgcag gaaagccagt gcagggcacc   420
agctttcatt tttttctgt cggggggag gctttagaat tacaggggt ggtttttaat      480
tacagaacaa cgtacccaga cggaacaatt tttccaaaga atgcaacagt gcaatctcaa   540
gtaatgaaca cagagcacaa ggcgtaccta gataagaaca aagcatatcc tgttgaatgt   600
tgggttcctg atcccaccag aaatgaaaac acaagatatt ttgggacact aacaggagga   660
gaaaatgttc ctccagttct tcatataaca aacactgcca caacagtgct gctggatgaa   720
tttggtgttg ggccactttg caaaggtgac aacttgtatt tgtcagctgt tgatgtttgt   780
ggcatgttta ctaacagatc tggttcccag cagtggagag gactgtccag atattttaag   840
gttcagctaa gaaaaaggag ggttaaaaac ccctacccaa tttcttttct tcttactgat   900
ttaattaaca gaaggacccc tagagttgat gggcagccta tgtatggcat ggatgctcag   960
gtagaggagg ttagagtttt tgaggggaca gaggaacttc caggggaccc agacatgatg  1020
agatatgttg acagatatgg acagttgcag acaaagatgc tgtaa                  1065
```

<210> SEQ ID NO 25
<211> LENGTH: 1065
<212> TYPE: DNA
<213> ORGANISM: Artificial Sequence
<220> FEATURE:
<223> OTHER INFORMATION: Codon-optimized JCV genotype 2A VP1 coding
      sequence

<400> SEQUENCE: 25

| | | | | | | |
|---|---|---|---|---|---|---|
| atggcaccca | caaagcgcaa | gggcgaacgc | aaggacccag | tccaggtccc | caagttgctg | 60 |
| atcaggggcg | gcgtggaggt | cctggaggtc | aagaccggcg | tggactccat | caccgaggtg | 120 |
| gagtgtttct | tgacacccga | gatgggcgac | cccgacgagc | acctgcgcgg | gttcagcaag | 180 |
| agcatcagca | tcagcgacac | attcgagtcc | gactcaccca | ataaggacat | gttgccatgc | 240 |
| tattccgtcg | cccgcatccc | actgcccaac | ctcaacgaag | acttgacatg | cggcaacatc | 300 |
| ctgatgtggg | aagccgtcac | actgaagacc | gaagtcatcg | gcgtcaccac | cctgatgaat | 360 |
| gtgcactcca | acggccaagc | gacgcacgac | aacgcgcccg | gaagccagtc | caggggaca | 420 |
| agcttccatt | tcttcagcgt | cggcggcgag | gcactcgagc | tgcaaggcgt | ggtgttcaac | 480 |
| tatcgcacca | gtatcccga | cggcaccata | ttccccaaga | cgcaaccgt | ccaaagtcag | 540 |
| gtcatgaaca | ccgagcacaa | agcatatctc | gataagaata | aggcctaccc | cgtcgagtgt | 600 |
| tgggtccccg | atccaaccag | gaacgagaac | acccgctact | tcggcaccct | gaccggcggc | 660 |
| gagaacgtcc | cacccgtgtt | gcacatcaca | ataccgcca | caaccgtcct | gctcgacgag | 720 |
| ttcggcgtcg | gcccactctg | caaggagac | aacctctacc | tgagcgccgt | cgacgtctgc | 780 |
| ggaatgttca | ccaatcgaag | cggcagccag | caatggcgcg | ggttgtcccg | ctacttcaaa | 840 |
| gtccagctcc | gcaagcgccg | cgtgaagaat | ccctatccaa | tcagtttcct | gctgaccgat | 900 |
| ttgatcaatc | gccgcacacc | acgcgtcgac | ggccagccca | tgtacggcat | ggacgcccaa | 960 |
| gtcgaagaag | tgcgcgtatt | cgaggggacc | gaggagttgc | ccggcgatcc | cgacatgatg | 1020 |
| cgctacgtcg | atcgctacgg | ccagctccaa | accaagatgc | tatga | | 1065 |

<210> SEQ ID NO 26
<211> LENGTH: 1065
<212> TYPE: DNA
<213> ORGANISM: Artificial Sequence
<220> FEATURE:
<223> OTHER INFORMATION: Codon-optimized JCV genotype 3B VP1 coding
      sequence

<400> SEQUENCE: 26

| | | | | | | |
|---|---|---|---|---|---|---|
| atggcaccca | caaagcgcaa | gggcgaacgc | aaggacccag | tccaggtccc | caagttgctg | 60 |
| atcaggggcg | gcgtggaggt | cctggaggtc | aagaccggcg | tggactccat | caccgaggtg | 120 |
| gagtgtttct | tgacacccga | gatgggcgac | cccgacgagc | acttgcgcgg | gttttcgaag | 180 |
| agcatcagca | tcagcgacac | attcgagtcc | gactcaccca | ataaggacat | gttgccatgc | 240 |
| tattccgtcg | cccgcatccc | actgcccaac | ctcaacgaag | acttgacatg | cggcaacatc | 300 |
| ctgatgtggg | aagccgtcac | actgaagacc | gaagtcatcg | gcgtcaccac | cctgatgaat | 360 |
| gtgcactcca | acggccaagc | gacgcacgac | aacgcgcccg | gaagccagtc | caggggaca | 420 |
| agcttccatt | tcttcagcgt | cggcggcgag | gcactcgagc | tgcaaggcgt | ggtgttcaac | 480 |
| tatcgcacca | gtatcccga | cggcaccata | ttccccaaga | cgcaaccgt | ccaaagtcag | 540 |
| gtcatgaaca | ccgagcacaa | agcatatctc | gataagaata | aggcctaccc | cgtcgagtgt | 600 |

-continued

```
tgggtccccg atccaaccag gaacgagaac acccgctact tcggcaccct gaccggcggc    660
gagaacgtcc cacccgtgtt gcacatcaca ataccgcca caaccgtcct gctcgacgag    720
ttcggcgtcg gcccactctg caagggagac aacctctacc tgagcgccgt cgacgtctgc    780
ggaatgttca ccaatcgaag cggcagccag caatggcgcg ggttgtcccg ctacttcaaa    840
gtccagctcc gcaagcgccg cgtgaagaat ccctatccaa tcagtttcct gctgaccgat    900
ttgatcaatc gccgcacacc acgcgtcgac ggccagccca tgtacggcat ggacgcccaa    960
atcgaagaag tgcgcgtatt cgaggggacc gagcagttgc ccggcgatcc cgacatgatg   1020
cgctacgtcg atcgctacgg ccagctccaa accaagatgc tatga                   1065
```

<210> SEQ ID NO 27
<211> LENGTH: 354
<212> TYPE: PRT
<213> ORGANISM: JC virus

<400> SEQUENCE: 27

```
Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Leu Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
```

```
           290                 295                 300
Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Lys Tyr Gly Gln Leu Gln Thr Lys
                340                 345                 350

Met Leu
```